United States Patent
Weis et al.

(10) Patent No.: US 11,304,356 B2
(45) Date of Patent: Apr. 19, 2022

(54) HIGH THROUGHPUT CASSETTE FILLER

(71) Applicant: Monsanto Technology LLC, St. Louis, MO (US)

(72) Inventors: Matthew J. Weis, St. Louis, MO (US); Michael Dayawon, St. Louis, MO (US); Scott Essner, St. Louis, MO (US); Cheryl Florida, St. Louis, MO (US); Alan Jackson, St. Louis, MO (US); Jeffrey A. Lickenbrock, St. Louis, MO (US); Mark J. Menius, St. Louis, MO (US); Ryan K. Tellor, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1048 days.

(21) Appl. No.: 15/735,071

(22) PCT Filed: Jun. 7, 2016

(86) PCT No.: PCT/US2016/036236
§ 371 (c)(1),
(2) Date: Dec. 8, 2017

(87) PCT Pub. No.: WO2016/200825
PCT Pub. Date: Dec. 15, 2016

(65) Prior Publication Data
US 2018/0317375 A1 Nov. 8, 2018

Related U.S. Application Data

(60) Provisional application No. 62/172,576, filed on Jun. 8, 2015.

(51) Int. Cl.
*A01C 1/04* (2006.01)
*G06M 7/08* (2006.01)
(Continued)

(52) U.S. Cl.
CPC .......... *A01C 1/046* (2013.01); *A01C 1/04* (2013.01); *A01H 1/04* (2013.01); *B07C 5/08* (2013.01);
(Continued)

(58) Field of Classification Search
CPC ....... B07C 5/08; B07C 2501/009; A01C 1/04; A01H 1/04; G01N 35/04; G06M 7/08;
(Continued)

(56) References Cited

U.S. PATENT DOCUMENTS

| 7,502,113 B2 | 3/2009 | Deppermann et al. |
| 7,591,101 B2 | 9/2009 | Deppermann |

(Continued)

FOREIGN PATENT DOCUMENTS

| WO | 2014151183 A1 | 9/2014 |
| WO | 2016044050 A1 | 3/2016 |
| WO | 2016049408 A1 | 3/2016 |

OTHER PUBLICATIONS

International Search Report from corresponding PCT/US2016/036236 dated Aug. 30, 2016.

*Primary Examiner* — Patrick H Mackey
(74) *Attorney, Agent, or Firm* — Sandberg Phoenix & von Gontard P.C.

(57) ABSTRACT

A high throughput system for sorting a plurality of different small object types into a plurality of cells of a plurality of small object cassettes is provided. The system comprises: at least one small object cassette having a plurality of small object cells; an automated conveyor system for transporting the cassette(s) from a loading location to a unloading location on the conveyor system; at least one cassette filling station disposed over the conveyor system such that the conveyor system extends under a small object distribution subsystem of each respective cassette filling station; and a
(Continued)

computer based central control system structured and operable to control various operations of the conveyor system and each cassette filling station.

20 Claims, 18 Drawing Sheets

(51) Int. Cl.
*B07C 5/08* (2006.01)
*A01H 1/04* (2006.01)
*G01N 35/04* (2006.01)

(52) U.S. Cl.
CPC .............. *G01N 35/04* (2013.01); *G06M 7/08* (2013.01); *A01C 2001/048* (2013.01); *B07C 2501/009* (2013.01); *C12Q 2600/156* (2013.01)

(58) Field of Classification Search
CPC ..... C12Q 2600/156; B65B 35/30; B65B 5/10; B65B 5/101; B65B 5/103
See application file for complete search history.

(56) References Cited

U.S. PATENT DOCUMENTS

| | | | |
|---|---|---|---|
| 7,611,842 B2 | 11/2009 | Deppermann et al. | |
| 7,703,238 B2 | 4/2010 | Deppermann et al. | |
| 7,767,883 B2 | 8/2010 | Deppermann et al. | |
| 7,830,516 B2 | 11/2010 | Deppermann et al. | |
| 7,832,143 B2 | 11/2010 | Deppermann et al. | |
| 7,849,632 B2 | 12/2010 | Deppermann et al. | |
| 7,877,926 B2 | 2/2011 | Deppermann | |
| 7,886,506 B2 * | 2/2011 | Knoth | G07F 17/0092 53/475 |
| 7,941,969 B2 | 5/2011 | Deppermann et al. | |
| 7,998,669 B2 | 8/2011 | Deppermann et al. | |
| 8,028,469 B2 | 10/2011 | Deppermann et al. | |
| 8,071,845 B2 | 12/2011 | Deppermann et al. | |
| 8,230,662 B2 * | 7/2012 | Boutin | G07F 17/0092 53/55 |
| 8,245,439 B2 | 8/2012 | Deppermann et al. | |
| 8,312,672 B2 | 11/2012 | Deppermann et al. | |
| 8,406,916 B2 * | 3/2013 | Bentele | B65B 35/18 700/216 |
| 8,434,259 B2 | 5/2013 | Deppermann | |
| 8,436,225 B2 | 5/2013 | Deppermann et al. | |
| 8,443,545 B2 | 5/2013 | Deppermann et al. | |
| 8,539,713 B2 | 9/2013 | Deppermann et al. | |
| 8,561,346 B2 | 10/2013 | Deppermann et al. | |
| 8,959,833 B2 | 2/2015 | Deppermann et al. | |
| 8,997,398 B2 | 4/2015 | Deppermann et al. | |
| 9,003,696 B2 | 4/2015 | Deppermann et al. | |
| 9,027,278 B2 | 5/2015 | Deppermann et al. | |
| 9,364,397 B2 * | 6/2016 | Shibasaki | A61J 7/0076 |
| 9,658,176 B2 | 5/2017 | Dai et al. | |
| 10,934,032 B2 * | 3/2021 | Kames | B65B 5/105 |
| 2004/0154688 A1 * | 8/2004 | Geltser | B65B 57/20 141/2 |
| 2005/0224510 A1 | 10/2005 | Remis et al. | |
| 2006/0042527 A1 * | 3/2006 | Deppermann | G01N 35/00029 111/171 |
| 2008/0017661 A1 | 1/2008 | Hutchinson et al. | |
| 2011/0282488 A1 * | 11/2011 | Horev | G06M 7/00 700/232 |

* cited by examiner

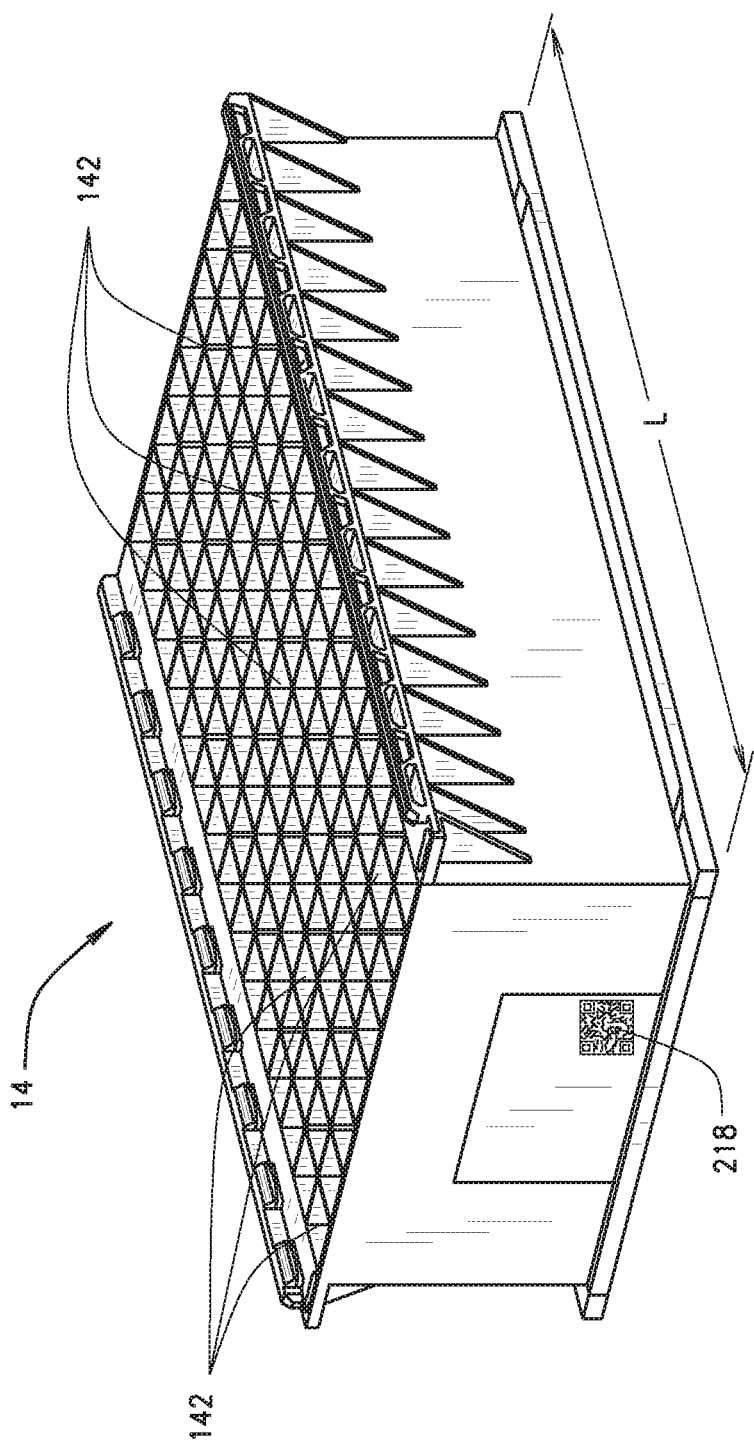

HIGH THROUGHPUT CASSETTE FILLER

CROSS-REFERENCE TO RELATED APPLICATIONS

This application is a National Stage of International Application No. PCT/US2016/036236, filed Jun. 7, 2016, which is a PCT International Application of U.S. Application No. 62/172,576, filed on Jun. 8, 2015, the disclosures of which are incorporated herein by reference in their entirety.

FIELD

The present teachings relate to an automated system and method for parsing groups of small objects, such as seeds, from a plurality of bulk quantities of different types of small objects and depositing the parsed groups of small objects into cells of a small object cassette.

BACKGROUND

The statements in this section merely provide background information related to the present disclosure and cannot constitute prior art.

The parsing and sorting of small agricultural, manufactured and/or produced objects such as seeds, pharmaceutical tablets or capsules, small electrical components, ball bearings, small food products, etc., from bulk quantities of such small objects can be cumbersome, painstakingly tedious, and wrought with human error.

For example, in plant breeding, selected quantities of various types of seeds, e.g., various hybrid types of seed, must be culled from large numbers of such seed types, deposited in suitable containers, e.g., seed cassettes, and then transferred to a storage facility and/or to the field for planting. Generally, the selected amounts of seeds are manually separated from bulk quantities of the selected types of seeds and then manually packaged for transfer to a storage facility or to the field for planting. Hence, such sorting processes are typically painstakingly performed by hand, which is extremely time consuming and subject to human error. More particularly, with regard to plant breeding, the use of cassette planting technology is rapidly expanding throughout the plant breeding industry. As cassette planting becomes more widespread, the need to rapidly load seed into the cassettes becomes more pressing.

SUMMARY

The present disclosure provides a system and method for filling cassettes comprising a plurality of cells with small objects, e.g., seeds, at a high throughput rate. In various embodiments, the system will be configured in a large centralized filling location where all cassette filling for an entire operation is performed, resulting in large amounts of bulk small objects coming into, and large numbers of filled cassettes going out of, a central warehouse. The cassettes are then distributed to the various field locations for planting.

For example, in various embodiments, it is envisioned that the present cassette filling system will be able to fill 500,000 to 1,000,000, e.g., 750,000, cassette cells in a two month timeframe. For example, in various implementations each cassette can have 100 to 160 cells, e.g., 120 cells, wherein each cell can hold approximately 100 to 150, or more small objects, e.g., 125 corn seeds, depending on size of the cells and the small objects. In such implementations, various types of small objects, e.g., various hybrid types of seeds, are loaded into the cassette cells based on pre-established object map files that list the object type, e.g., hybrid type, versus a cassette designator and cell number within the respective designated cassette. In various implementation a two-dimensional (2D) barcode sticker can be attached to each cassette to identity each respective cassette. After the cells of the cassettes are filled by the cassette filling system, the filled cassettes can be shipped to a desired location. For example, in the case of seeds, the filled cassettes can be shipped to a warehouse and/or the field in large shipping crates, whereafter the cassettes can be implemented into various planting systems, machines or vehicles.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 2A is an isometric view of an exemplary small object cassette of the system shown in FIG. 1, in accordance with various embodiments of the present disclosure.

Corresponding reference numerals indicate corresponding parts throughout the several views of drawings.

DETAILED DESCRIPTION

Figure 1:
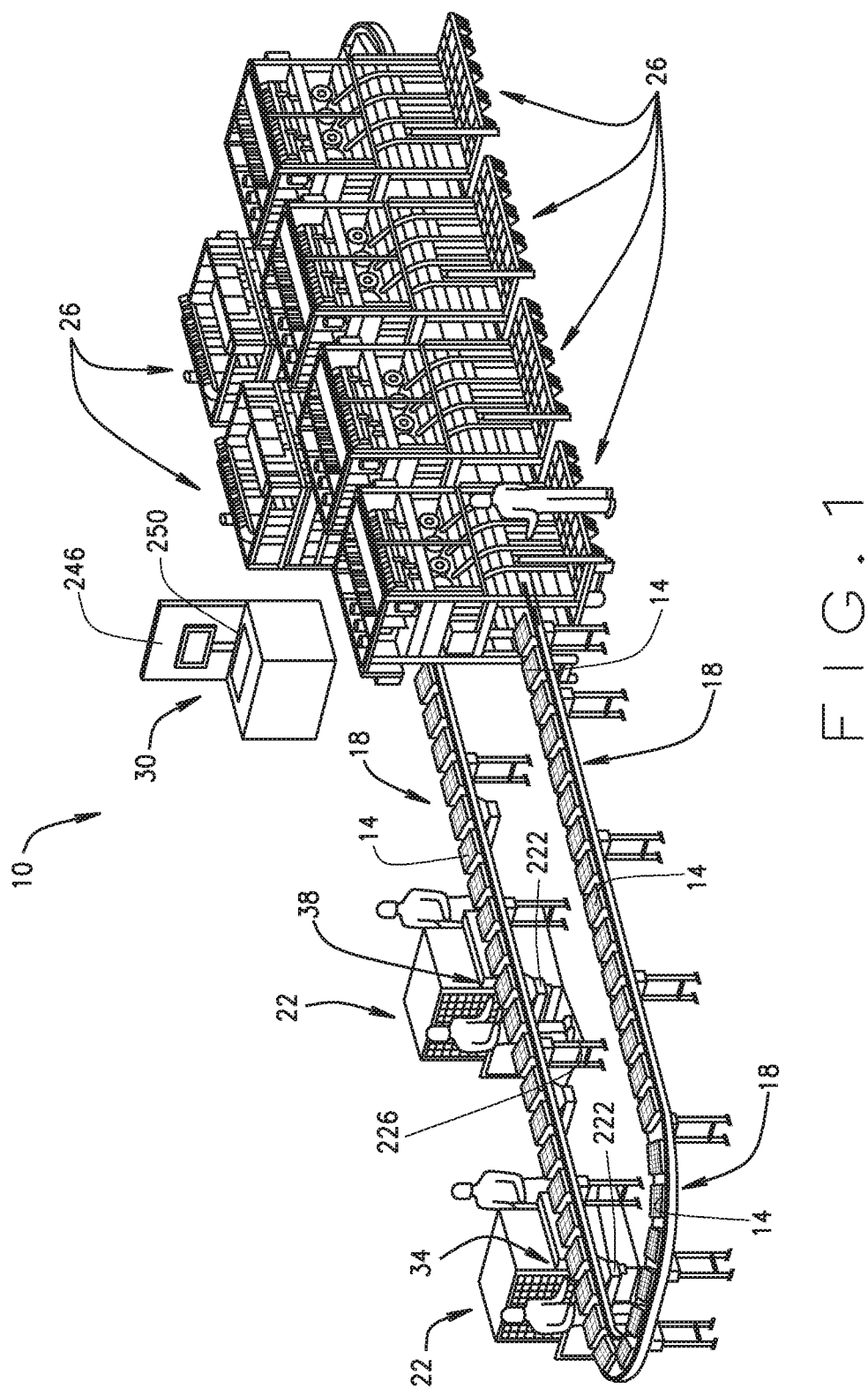
FIG. 1 is an isometric view of a high throughput system for sorting a plurality of different small object types into a plurality of cells of a plurality of small object cassettes, in accordance with various embodiments of the present disclosure.

The following description is merely exemplary in nature and is in no way intended to limit the present teachings, application, or uses. Throughout this specification, like reference numerals will be used to refer to like elements. Additionally, the embodiments disclosed below are not intended to be exhaustive or to limit the invention to the precise forms disclosed in the following detailed description. Rather, the embodiments are chosen and described so that others skilled in the art can utilize their teachings. More particularly, the following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims.

Unless otherwise defined, all technical and scientific terms used herein have the same meaning as commonly understood by one of ordinary skill in the art to which this disclosure belongs. The terminology used herein is for the purpose of describing particular example embodiments only and is not intended to be limiting. As used herein, the singular forms "a," "an," and "the" can be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. Any method steps, processes, and operations described herein are not to be construed as necessarily requiring their performance in the particular order discussed or illustrated, unless specifically identified as an order of performance. It is also to be understood that additional or alternative steps can be employed.

When an element or layer is referred to as being "on," "engaged to or with," "connected to or with," or "coupled to or with" another element, device, object, etc., it can be directly on, engaged, connected or coupled to or with the other element, device, object, etc., or intervening elements, devices, objects, etc., can be present. In contrast, when an element is referred to as being "directly on," "directly engaged to," "directly connected to," or "directly coupled to" another element, device object, etc., there can be no intervening elements, devices, objects, etc., present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, devices, objects, sections, etc., these elements, components, regions, devices, objects, sections, etc., should not be limited by these terms. These terms can only be used to distinguish one element, component, region, device, object, section, etc., from another region, device, object, section etc., and do not imply a sequence or order unless clearly indicated by the context.

The term code, as used herein, can include software, firmware, and/or microcode, and can refer to one or more programs, routines, functions, classes, and/or objects. The term shared, as used herein, means that some or all code from multiple modules can be executed using a single (shared) processor. In addition, some or all code from multiple modules can be stored by a single (shared) memory. The term group, as used above, means that some or all code from a single module can be executed using a group of processors. In addition, some or all code from a single module can be stored using a group of memories.

The apparatuses and methods described herein can be implemented by computer code executed by one or more processors. The code includes processor-executable instructions that are stored on a non-transitory, tangible, computer readable medium. The computer code can also include stored data. Non-limiting examples of the non-transitory, tangible, computer readable medium are nonvolatile memory, magnetic storage, and optical storage.

Referring to FIG. 1, in various embodiments, the present disclosure provides a high throughput small object parsing and cassette filling system 10 that is structured and operable to parse a plurality of different types of small objects, e.g., different hybrids of seed, into a plurality of groups of small objects and deposit each group into cells of one or more small object cassettes 14. It should be understood that although the present system 10 and related methods described herein are applicable for the high throughput parsing and sorting of generally any small objects, such as small agricultural, manufactured and/or produced objects, for example, seeds, pharmaceutical tablets or capsules, small electrical components, ball bearings, small food products, etc., for simplicity the present system 10 and related methods will be exemplarily described herein with regard to the parsing and sorting of seeds.

In various embodiments, the system 10 generally comprises an automated conveyor system 18, one or more cassette processing stations 26, and a central control system 30 for directly and indirectly controlling and coordinating all automated and cooperative functions and operations of the system 10. It is envisioned that the conveyor system 18 can be any system (human, automated, robotic, etc.) suitable for conveying cassettes 14 from one processing station 26 to another, as described below, for clarity and simplicity, the conveyor system 18 will be exemplarily described and illustrated herein as a conveyor track, and referred to as the conveyor track 18. Also, although the cassette processing stations 26 can be structured and operable to perform many different operations, procedures and analysis on the cassettes 14 and or small objects deposited therein, as described below, for clarity and simplicity, the processing stations 26 will be exemplarily described and illustrated herein as a cassette filling stations, and referred to as the cassette filling stations 26.

In various embodiments, the system 10 additionally includes at least one load-unload station 22 located next to the conveyor track 18. The automated conveyor track 18 is structured and operable to transport the cassette(s) 14 from a loading location 34 on the conveyor track 18 to an unloading location 38 on the conveyor track 18. The load-unload station(s) 22 is/are located next to the conveyor track 18 adjacent the loading and unloading locations 34 and 38. It should be noted that in various embodiments, the loading location 34 and the unloading location 38 can be substantially the same location on the track 18. Each load-unload station 22 is structured and operable to assist and operator in loading and/or unloading the cassette(s) 14 onto and off of the conveyor track 18. In various implementations, the cassette filling station(s) 26 is/are disposed over the conveyor track 18 such that the conveyor track 18 extends through each cassette filling station 26 and under a small object distribution subsystem 42 of each respective cassette filling station 26.

The central control system 30 comprises a computer-based system communicatively connected to at least the conveyor track 18 and each of the cassette filling station(s) 26, whereby the central control system 30 is structured and operable to control and coordinate the various operations of the conveyor track 18 and each cassette filling station 26 via execution of cassette filling code, as described herein. It should be understood that although the central control system 30 is sometimes described herein as directly controlling the various automated, or robotic, operations of the small object parsing and cassette filling system 10, it is the execution of the cassette filling code, e.g., execution of the software, programs and/or algorithms, by at least one processor of the control system 30 using inputs from a user interface, various electronically stored date table, databases, lookup table, etc., and various other components, sensors, systems and assemblies of the system 10 that actually control the various automated, or robotic, operations of the small object parsing and cassette filling system 10 described herein.

Referring now to FIGS. 1, 2A, 3, 4 and 5, in various embodiments, each cassette filling station 26 includes at least one small object counting and parsing subsystem 46 and the small object distribution subsystem 42. Each cassette filling station 26 additionally includes a vacuum system that is not described in detail herein and is structured and operable to transport the small objects from various places within the respective cassette filling station 26 to other places within the respective cassette filling station 26, as described herein. Each cassette filling station 26 further includes various valves, relays, actuators, circuits, etc., that are not described herein. Still further, each cassette filling station 26 includes various system support structures, e.g., bars, beams, struts, braces, etc., that are not described herein.

Although, the various components of the vacuum system, the various valves, relays, actuators, circuits, etc., and the various system support structures are not described in detail herein, and can or can not be shown in the various figures, such description and depiction are not necessary for a full understanding of the present disclosure by one skilled in the art, and their structure, location and function would be readily surmised and understood by one skilled in the art upon reading the present disclosure.

Figure 4:
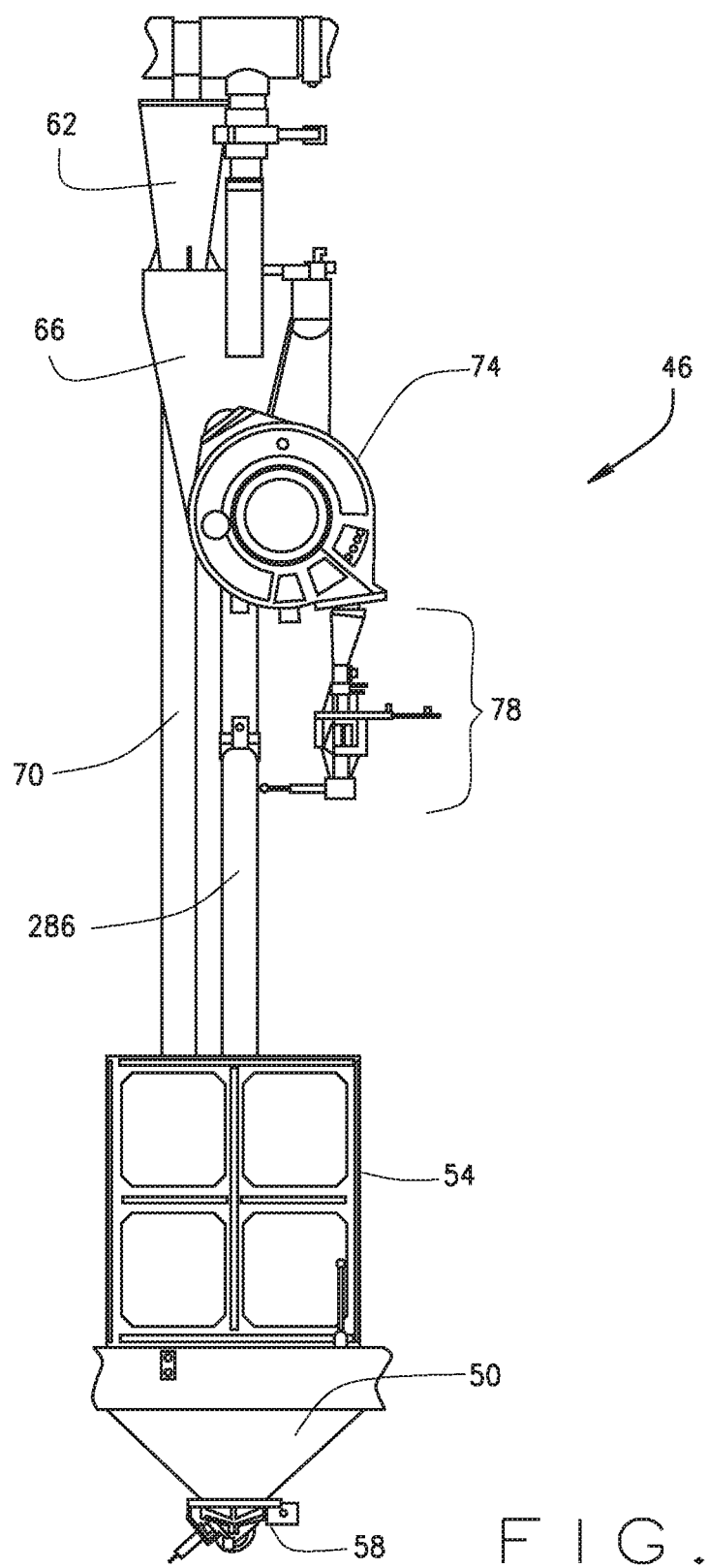
FIG. 4 is a front view of a small object counting and parsing subsystem of the cassette filling station shown in FIG. 3, in accordance with various embodiments of the present disclosure.

Referring particularly to FIG. 4, each small object counting and parsing subsystem 46 is structured and operable to count and parse a plurality of groups of small objects from a bulk quantity of the small objects. It should be understood that each small object counting and parsing subsystem 46 can count and parse a respective different type of small objects, e.g., a different hybrid of seed. Hence, a cassette filling station 26 comprising a plurality of small object counting and parsing subsystems 46 can be structured and operable to count and parse a plurality of groups of different types of small objects from bulk quantities of a plurality of different types of the small objects.

Each group of small objects comprises a respective number of the respective type of small objects stipulated by the control system 30, via execution of cassette filling code. Each small object counting and parsing subsystem 46 comprises a bulk small object bin 50 having a lockable lid 54 pivotally connected thereto. The bulk small object bin 50 is structured and operable to retain a bulk quantity of small objects of a selected type, e.g., a bulk quantity of a selected type of hybrid seed. In various embodiments, the bulk small object bin 50 includes an evacuation port 58 disposed at a bottom of the bin 50 that is structured and operable to controllably close, whereby the small objects are retained within the bin 50, and open, whereby the small objects can be evacuated from the bin 50. Each small object counting and parsing subsystem 46 additionally includes an object decelerator 62 and an upper small object bin 66 fluidly connected to the decelerator 62 such that small objects entering the decelerator (as described below) will flow into the upper small object bin 66 via the force of gravity. The decelerator 62 is fluidly connected to the bulk small object bin 50 by a vacuum conduit 70 that is structured and operable to transport a plurality of small objects from the bulk small object bin 50 to the decelerator, via a vacuum force provided by a vacuum subsystem (not shown) of the respective small object counting and parsing subsystem 26. The decelerator 62 is structured and operable to receive the small objects from the bulk small object bin 50, decelerate, or reduce, a speed of the small object being transported from the bulk small object bin 50, and deposit them into the upper small object bin 66.

The decelerator 62 can be any device or assembly suitable for decelerating the speed of the small objects (i.e., slowing the speed at which the small objects are traveling) received from the bulk small object bin 50. For example, in various embodiments, the decelerator 62 can be conical shaped receptacle having the vacuum conduit 70 fluidly connected to a top, larger circumference, portion of the conical decelerator 62, and the upper small object bin 66 fluidly connected to an open lower, apex, portion. To decelerate the speed of the small objects, the small object are transported from the bulk small object bin 50, via the vacuum conduit 70 and enter through the sidewall of the decelerator 62 at the top, larger circumference, portion. The speed of travel at which the small objects enter the decelerator 62 will cause the small objects to travel around the interior of the sidewall of the conical shaped decelerator 62 in a rotating, or vortex, flow. Subsequently, due to friction and the force of gravity, the small objects will migrate down the sidewall as their speed of travel reduces, and they will eventually drop through the open apex into the upper small object bin 66, whereafter the small objects are temporarily retained.

In various embodiments, the upper small object bin 66 can be funnel shaped such that the small objects received from the decelerator 62 at a top end of the upper small object bin 66 will be funneled down, via the force of gravity, toward a narrower open lower end. Each small object counting and parsing subsystem 46 further includes a small object singulator and counter 74 fluidly connected to the open lower end of the upper small object bin 66, and a small object queuing assembly 78 fluidly connected to the small object singulator and counter 74. The small object singulator and counter 74 is structured and operable to extract small objects from the upper small object bin 66 via a singulation device, e.g., a vacuum wheel (not shown), count the small objects, and parse the small objects into the groups of small objects wherein each group of small objects comprises a respective number of small objects stipulated by execution of the cassette filling code by the central control system. In various embodiments, the small object singulator and counter 74 can comprise a singulating vacuum wheel unit, such as that described in U.S. Pat. No. 8,925,762, titled, High Speed Counter, issued Jan. 6, 2015 and assigned to the assignee of the present disclosure, the disclosure of which is incorporated by reference herein. The small object queuing assembly 78 is structured and operable to receive the groups of small objects from the small object singulator and counter 74 and deposit each group of small objects into the small object distribution subsystem 42, as described below.

Figure 5:
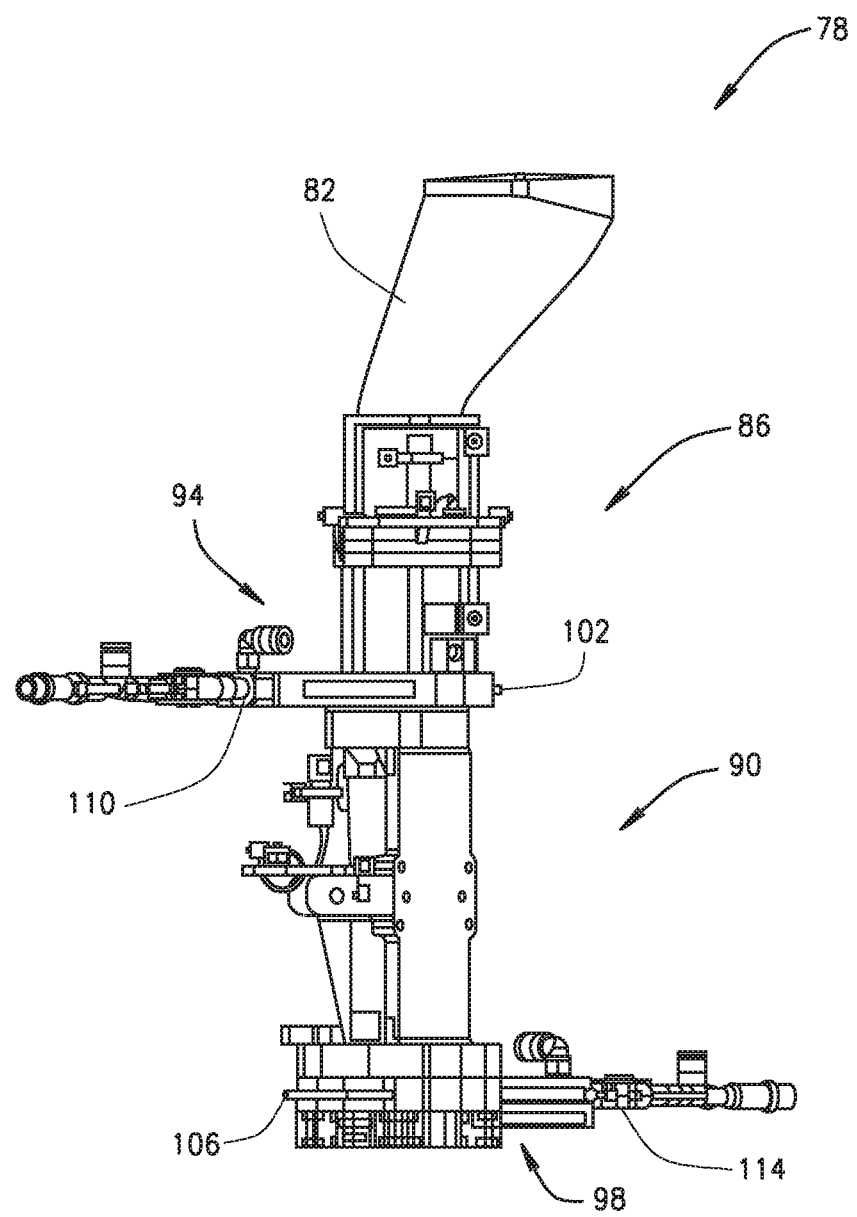
FIG. 5 is an isometric view of a small object queuing assembly of the small object counting and parsing subsystem shown in FIG. 4, in accordance with various embodiments of the present disclosure.

Referring particularly to FIG. 5, in various embodiments, the small object queuing assembly 78 includes a feeder funnel 82, a first queuing stage 86 fluidly connected to the feeder funnel 82 and a second queuing stage 90 fluidly connected to the first queuing stage 86. The first queuing stage 86 is structured and operable to receive and temporarily retain each group of small objects parsed by the small object singulator and counter 74. The second queuing stage 90 is fluidly connected to the first queuing stage 86 and is structured and operable to receive and temporarily retain each group of small objects from the first queuing stage 86. More specifically, the first queuing stage 86 comprises a hollow receptacle having an open top fluidly connected to the feeder funnel 82, and an open bottom fluidly connected to the second queuing stage 90, an interior chamber disposed between the open top and the open bottom, and a first sluice gate device 94 that is structure and operable (e.g., electrically, pneumatically, hydraulically, or mechanically), as controlled by the control system 30, to open and close the open bottom of the first queuing stage 86, and thereby control the transfer of each group of small objects from the first queuing stage 86 to the second queuing stage 90. Similarly, the second queuing stage 90 comprises a hollow receptacle having an open top fluidly connected to the first queuing stage 86, an open bottom fluidly connectable, as controlled by the control system 30, to the small object distribution subsystem 42 (as described below), an interior chamber disposed between the open top and the open bottom, and a second sluice gate device 98 that is structure and operable (e.g., electrically, pneumatically, hydraulically, or mechanically), as controlled by the control system 30, to open and close the open bottom of the second queuing stage 90, and thereby control the transfer of each group of small objects from the second queuing stage 90 to the distribution subsystem 42.

The first and second sluice gate devices 94 and 98 respectively include a first and second sluice gate 102 and 106 that are sized, shaped, and fitted to cover the open bottom of the first and second queuing stages 86 and 90 when in a Closed position, and to uncover (or open) the open bottom of the bottom the first and second queuing stages 86 and 90 when in an Open position. Each of the first and second sluice gate devices 94 and 98 additionally respectively include a first and second actuator 110 and 114 connected to the respective first and second sluice gates 102 and 106. The first and second actuators 110 and 114 are structured and operable (e.g., electrically, pneumatically, hydraulically, or mechanically), as controlled by the control system 30, to move the respective first and second sluice gates 102 and 106 between the Open and Closed positions to controllably and timely move each parsed group of small objects from the singulator and counter 74, to the first queuing stage 86, to the second queuing stage 90, to the distribution subsystem 42, more particularly, to a third queuing stage 134 of the distribution subsystem 42 (described below).

In operation, an initial or first group of small objects is parsed by the singulator and counter 74 from the quantity of small objects transported from the bulk small object bin 50 to the upper small object bin 66. The first group of parsed small objects are then deposited by the singulator and counter 74 into the first queuing stage 86 having the first sluice gate 102 in the Closed position such that the first group of small objects is retained within the first queuing stage 86. Subsequently, and prior to a subsequent or second group of small objects being parsed and deposited into the first queuing stage 86, the first sluice gate 102 is moved to the Open position, as controlled by the control system 30, such that the first group of small objects is transferred from (e.g., falls from) the first queuing stage 86 to the second queuing stage 90 having the second sluice gate 106 in the Closed position such that the transferred first group of small objects is retained within the second queuing stage 90. The first sluice gate 102 is moved to the Closed position and second group of small objects is parse and deposited in the first queuing stage 86 by the singulator and counter 74. Prior to, substantially simultaneously with, or subsequent to the second group of small objects being parsed and deposited into the first queuing stage 86, the third queuing stage 134 is positioned under the second queuing stage 90 (as described below). Thereafter, the second sluice gate 106 is moved to the Open position, as controlled by the control system 30, such that the first group of small objects is transferred from (e.g., falls from) the second queuing stage 90 into the third queuing stage 134, having a third sluice gate 162 in the Closed position such that the transferred first group of small objects is retained within the third queuing stage 134.

After the first group of small objects is deposited in the third queuing stage 134, the second sluice gate 106 is moved to the Closed position, the second group of small objects is transferred from the first queuing stage 86 to the second queuing stage 90, and a third group of small objects is parsed and deposited into the first queuing stage 86 by the singulator and counter 74. Prior to, substantially simultaneously with, or subsequent to any of the above described parsing and transferring of the groups of small objects, the third queuing stage 134 is moved over one of a plurality of buffer cells 126 of a buffer tray 122 (described below), as selected and controlled by the control system 30, and the third sluice gate 162 is moved to the Open position such that the first group of small objects is transferred from (e.g., falls from)

the third queuing stage 134 into the selected buffer cell 126, as described further below. This process is repeated until all the buffer cells 126 in the buffer tray 122 identified/stipulated by the control system 30 have received a respective stipulated group of small objects to be deposited in a respective selected cassette 14 positioned under the buffer tray 122, as controlled by the control system 30, as described further below.

Referring now to FIGS. 1, 2A, 3, 6, 7 and 8, the small object distribution subsystem 42 of each cassette filling station 26 is structured and operable to receive each parsed group of small object from each of the respective small object counting and parsing subsystems 46 of the respective cassette filling station 26, i.e., from the second queuing stages 90 of each small object counting and parsing subsystems 46 of the respective cassette filling station 26, as generally described above. Additionally, the small object distribution subsystem 42 is structured and operable to deposit each parsed group of small objects generated by each of the small object counting and parsing subsystems 46 of the respective cassette filling station 26 into a respective one of a plurality of small object cells 142 (e.g., 120 small object cells), as stipulated by the control system 30, of each cassette 14 after each respective cassette 14 is positioned under the small object distribution subsystem 42, particularly under the buffer tray 122 of each small object distribution subsystem 42, via the conveyor track 18, as controlled by the control system 30.

In various embodiments, each distribution subsystem 42 includes a transport and small deposition assembly 118, the multi-cell buffer tray 122 comprising a plurality buffer cells 126 (e.g., 120 buffer cells) and a buffer tray sluice plate 130. The transport and small object deposition assembly 118 comprises at least one third queuing stage 134 mounted to an X-Y transport 138. As exemplarily illustrated in FIGS. 6 & 8, in various embodiments, the X-Y transport and small object deposition assembly 118 comprises two third queuing stages 134. Although, the X-Y transport and small object deposition assembly 118 can comprise one, two, three or more third queuing stages 134, for simplicity and clarity, the distribution subsystem 42 of each cassette filling station 26 will be described herein as including two third queuing stages 134 mounted to an X-Y transport 138 in a side-by-side fashion. In various embodiments, the X-Y transport and small object deposition assembly 118 comprises a queuing stage carriage 146 to which the third queuing stages 134 are mounted. The queuing stage carriage 146 is movably mounted to a X-axis transport 150 that is structured and operable, as controlled by the control system 30, to bi-directionally move the queuing stage carriage 146, and more particularly, the third queuing stages 134, along the longitudinal axis of the X-axis transport 150, i.e., in the $^+$X and $^-$X directions. In such embodiments, the X-axis transport 150 is movably mounted to a Y-axis transport 154 that is structured and operable, as controlled by the control system 30, to bi-directionally move the X-axis transport 150, and more particularly, the third queuing stages 134, along the longitudinal axis of the Y-axis transport 154, i.e., in the $^+$Y and $^-$Y directions.

The X-axis and Y-axis transports 150 and 154 can be any assembly, system or mechanism structured and operable to controllably move the third queuing stages 134 bi-directionally along the respective longitudinal axes of the X-axis and Y-axis transports 150 and 154, i.e., anywhere within and X-Y coordinate system defined by the X-axis and Y-axis transports 150 and 154. For example, the X-axis and Y-axis transports 150 and 154 can comprise pneumatically, hydraulically or electrically controlled threaded shaft systems, wire or cable pulley systems, piston systems, conveyor belt systems, linear motor systems, or any other suitable positioning system structured and operable to move the third queuing stages 134 along the lengths of the respective X-axis and Y-axis transports 150 and 154, as controlled by the control system 30. In various embodiments, the X-axis and Y-axis transports 150 and 154 comprise linear motors structured and operable to produce a controllable linear force exerted respectively on the queuing stage carriage 146 and the X-axis transport to controllably move the third queuing stages 134 anywhere within the X-Y coordinate grid defined by the X-axis and Y-axis transports 150 and 154.

Each third queuing stage 134 comprises a hollow receptacle having an open top, an open bottom, an interior chamber disposed between the open top and the open bottom, and a third sluice gate device 158 that is structure and operable (e.g., electrically, pneumatically, hydraulically, or mechanically), as controlled by the control system 30, to open and close the open bottom of the respective third queuing stage 134, and thereby control the transfer of each group of small objects from the third queuing stage 134 to a selected buffer cell 126 of the buffer tray 122, as described below. Each third sluice gate device 158 includes a third sluice gate 162 that is sized, shaped, and fitted to cover the open bottom of the third queuing stage 134 when in a Closed position, and to uncover (or open) the open bottom of the bottom the third queuing stage 134 when in an Open position. Each third sluice gate device 158 additionally includes a third actuator 166 connected to the respective third sluice gate 162. The third actuator 166 is structured and operable (e.g., electrically, pneumatically, hydraulically, or mechanically), as controlled by the control system 30, to move the third sluice gate 162 between the Open and Closed positions to controllably and timely move each parsed group of small objects received from the second queuing stage 90 to the respective buffer cell 126 of the buffer tray 122.

As described above, the buffer tray 122 comprises a plurality of buffer cells 126 that are structured to receive and temporarily retain parsed groups of small objects. Each buffer cell 126 has an open top (shown in FIG. 6) and an open bottom (shown in FIG. 7) that can be covered by the buffer tray sluice plate 130 (shown in FIG. 7 in an Open position). The buffer tray sluice plate 130 is sized, shaped, and fitted to cover the bottom of the buffer tray 122, and particularly, the open bottoms of all the buffer cells 126. Particularly, the buffer tray sluice plate 130 is connected to a sluice plate actuator (not shown) that is operable to selectively move the buffer tray sluice plate 130, as controlled by the control system 30, between a Closed position and an Open position. When in the Closed position, the buffer tray sluice plate 130 covers the open bottoms of all the buffer cells 130 to thereby retain the groups of small objects that have been deposited therein, as described above. When moved to the Open position, the buffer tray sluice plate 130 uncovers the open bottoms of all the buffer cells 126 such that the groups of small objects retained therein are transferred from (e.g., fall from) the buffer cells 126 into corresponding cassette cells 142 that has been position beneath the buffer tray 122 by the conveyor track 18, as controlled by the control system 30.

As described above, as each counting and parsing subsystem 46 is parsing a second or third group of small objects one of the third queuing stages 134 is positioned under the second queuing stage 90 of any one of the counting and parsing subsystems 46 of the respective cassette filling station 26. More particularly, the X-Y transport 138 is operated, as controlled by the control system 30, to move one of the third queuing stages along the X-axis transport 150, and move the X-axis transport 150 along the Y-axis transport 154 such that a selected one of the third queuing stages 134 is positioned below the respective selected second queuing stage 90. Thereafter, the second sluice gate 106 is moved to the Open position, as controlled by the control system 30, such that the first group of small objects is transferred from (e.g., falls from) the second queuing stage 90 to the third queuing stage 134, having a third sluice gate 162 in the Closed position such that the transferred first group of small objects is retained within the third queuing stage 134. Thereafter, the X-Y transport 138 is operated, as controlled by the control system 30, to move the third queuing stage 134 retaining the first group of small objects along the X-axis transport 150, and move the X-axis transport 150 along the Y-axis transport 154 such that the third queuing stage 134 retaining the first group of small objects is positioned over a designated or target buffer cell 126 of the buffer tray 122, as stipulated by the control system 30. Once positioned over the target buffer cell 126, the third sluice gate 162 is moved to the Open position such that the first group of small objects is transferred from (e.g., falls from) the third queuing stage 134 into the target buffer cell 126 of the buffer tray 122 having the buffer tray sluice plate 126 in the Closed position.

Figure 2B:
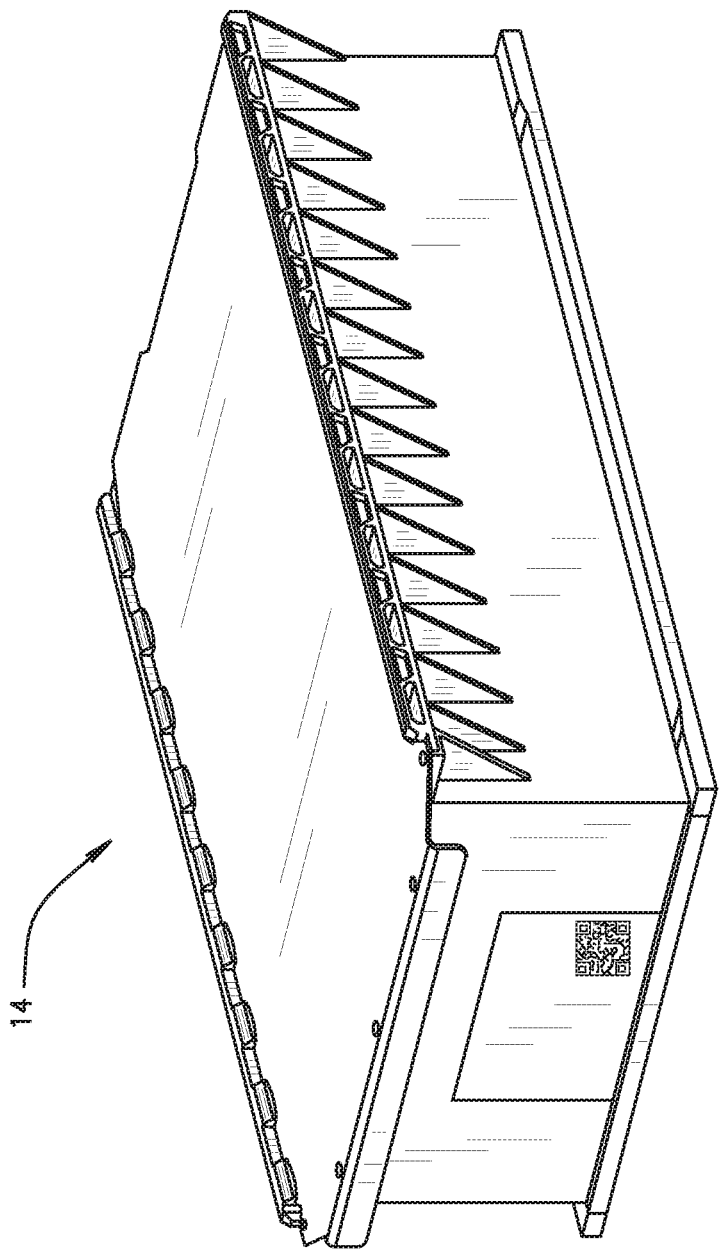
FIG. 2B is an isometric view of the small object cassette shown in FIG. 2A having a cassette cover disposed thereon, in accordance with various embodiments of the present disclosure.
Figure 2C:
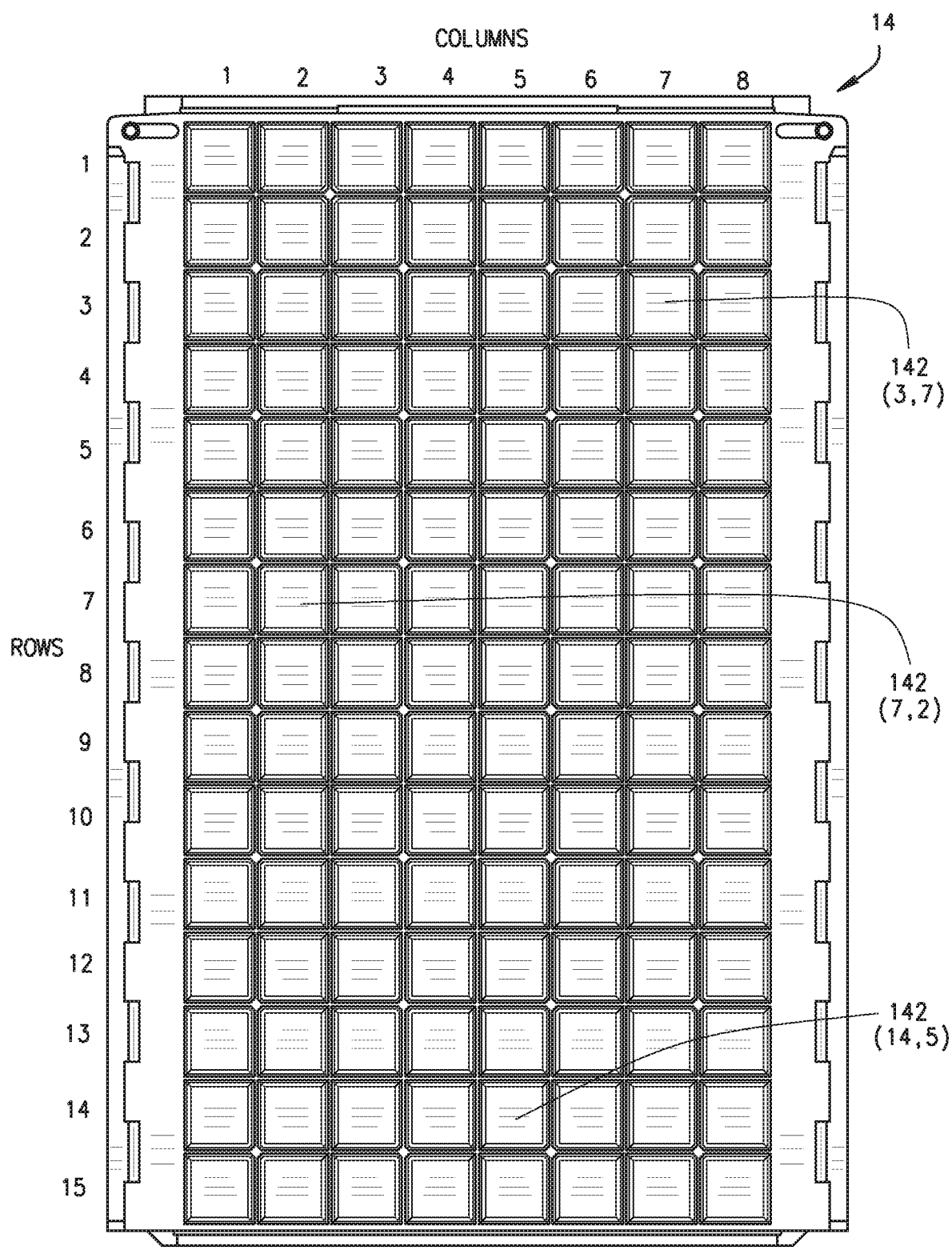
FIG. 2C is a top view of the small object cassette shown in FIGS. 2A and 2B, in accordance with various embodiments of the present disclosure.
Figure 3:
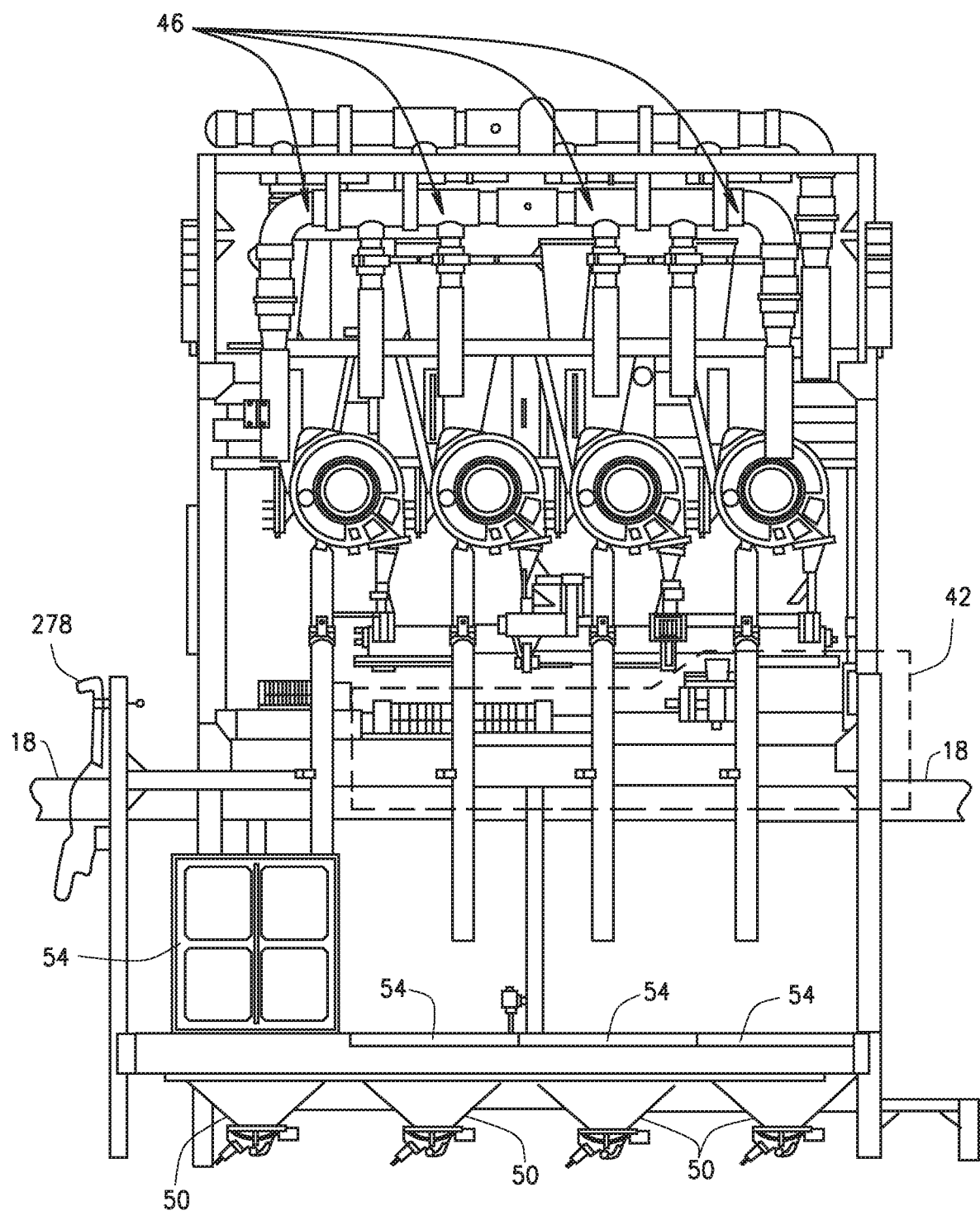
FIG. 3 is a front view of a cassette filling station of the system shown in FIG. 1, in accordance with various embodiments of the present disclosure.
Figure 6:
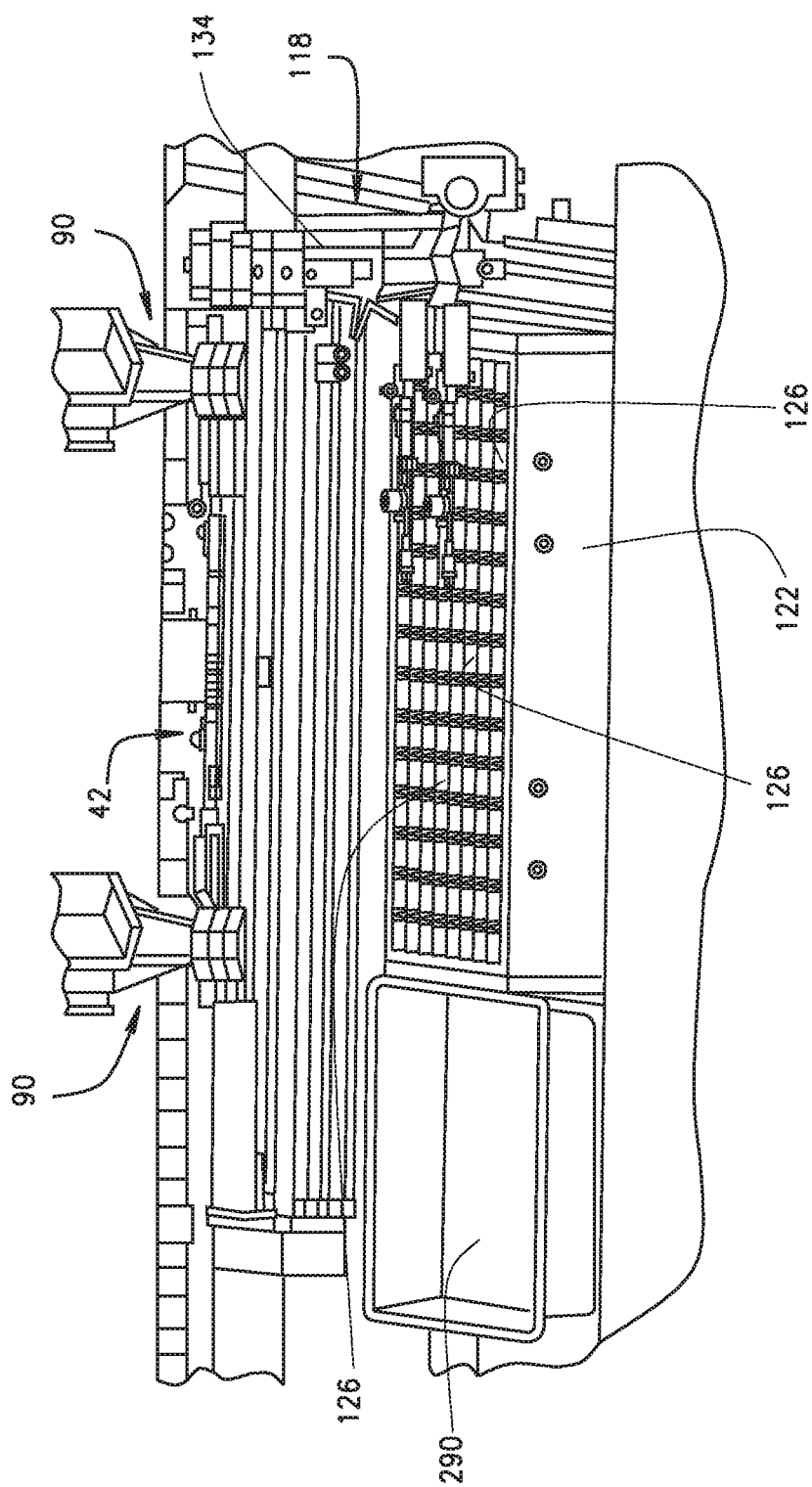
FIG. 6 is a top isometric view of a small object distribution subsystem of the cassette filling station shown in FIG. 3, in accordance with various embodiments of the present disclosure.
Figure 6A:
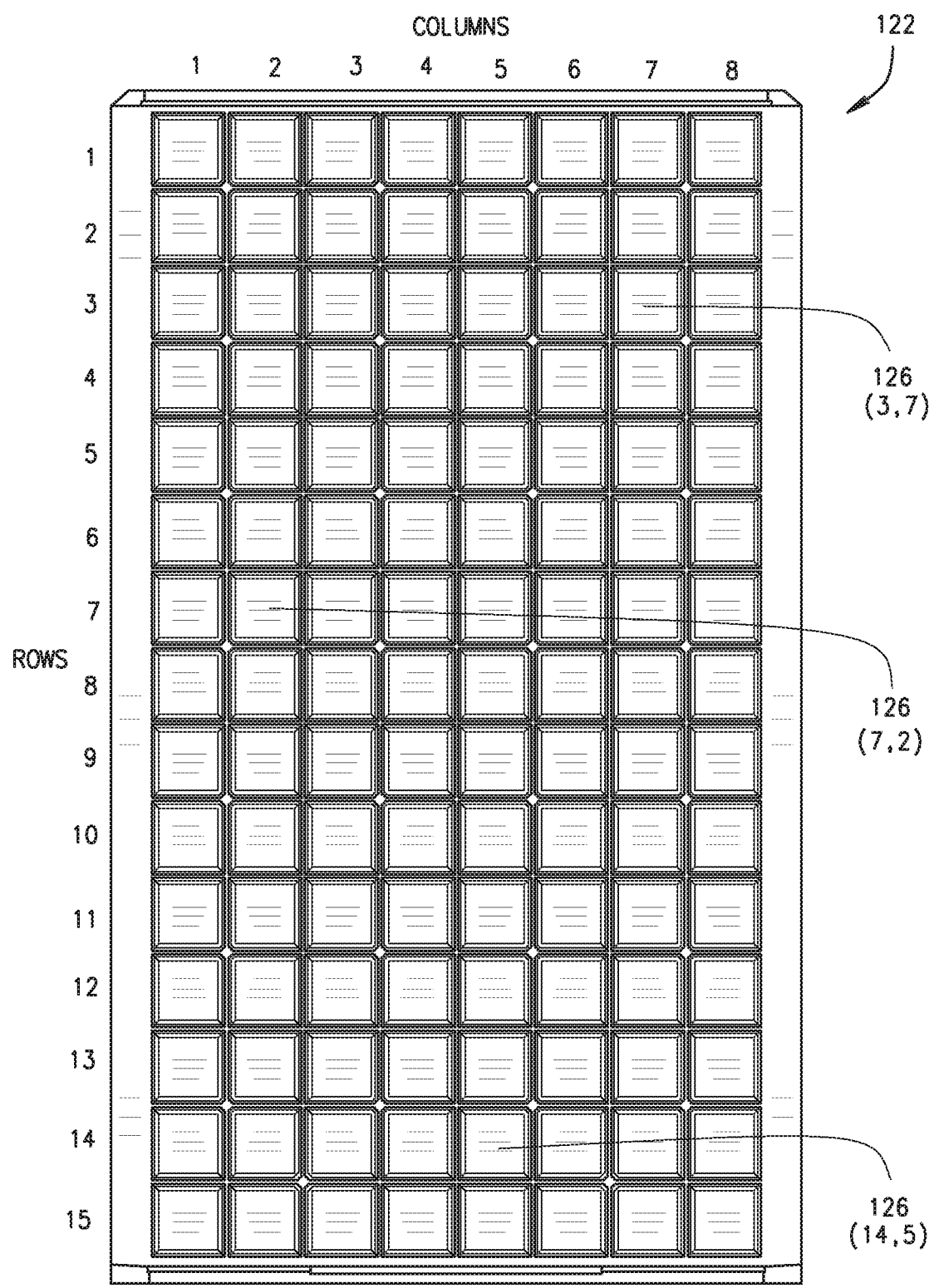
FIG. 6A is a top view of a buffer tray of the small object distribution subsystem shown in FIG. 6, in accordance with various embodiments of the present disclosure.
Figure 7:
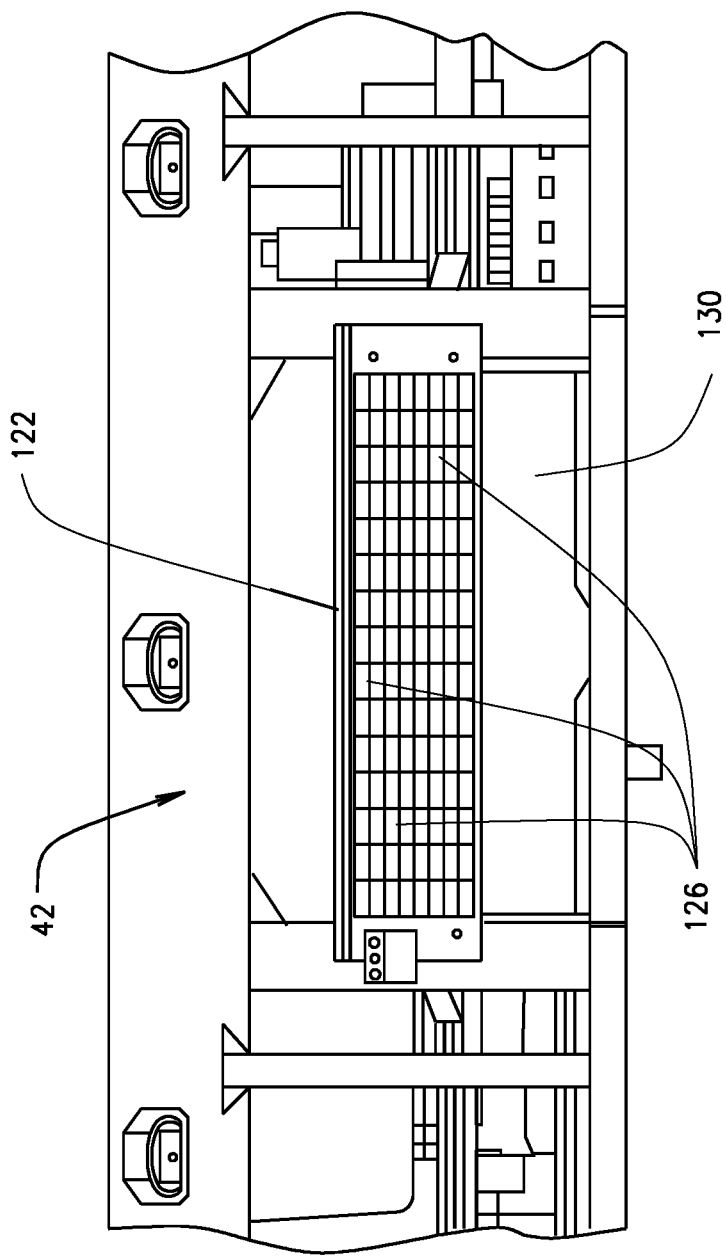
FIG. 7 is a bottom isometric view of the small object distribution subsystem shown in FIG. 6, in accordance with various embodiments of the present disclosure.
Figure 8:
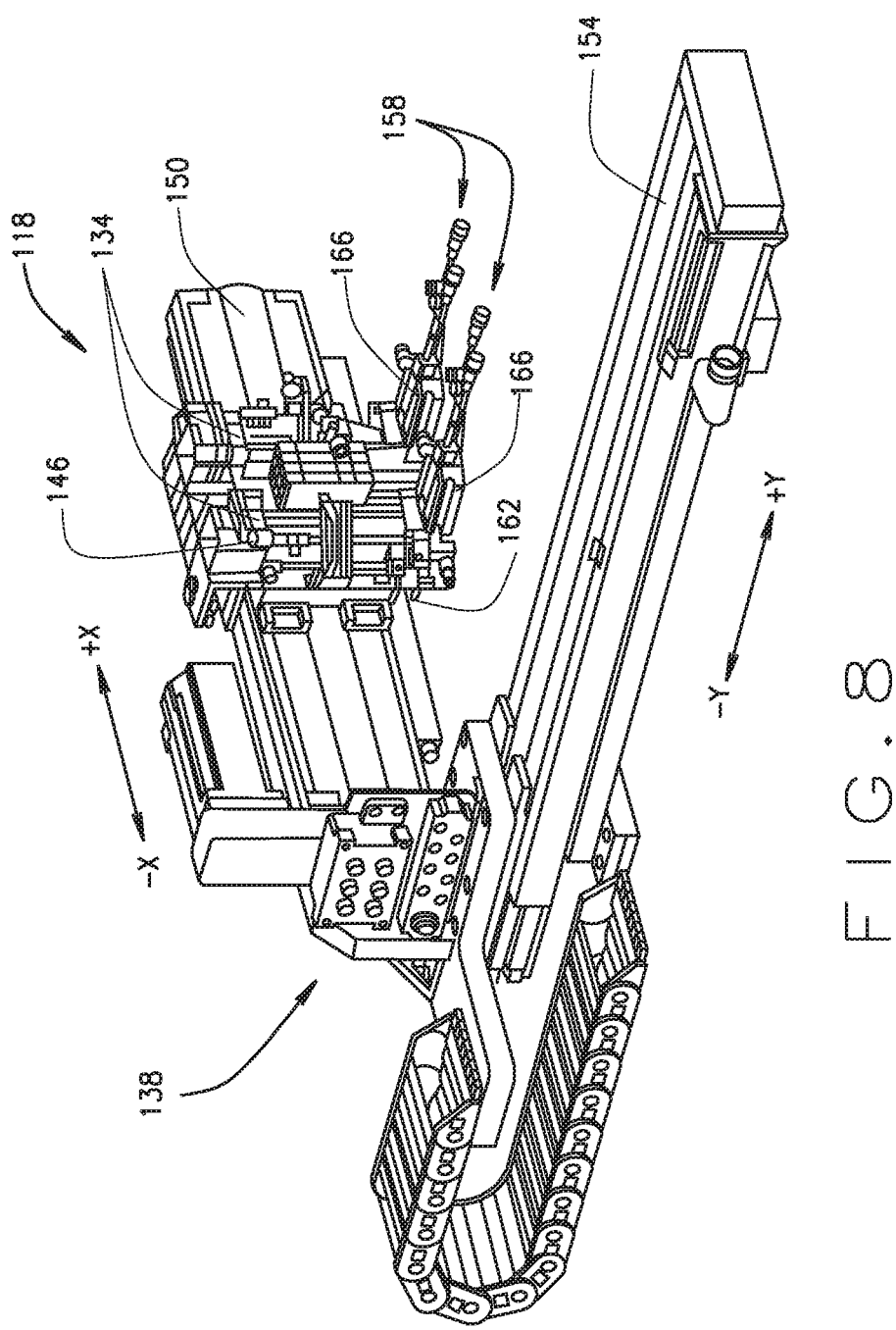
FIG. 8 is an isometric view of an X-Y transport and small object deposition assembly of the small object distribution subsystem shown in FIG. 6, in accordance with various embodiments of the present disclosure.

The process of parsing groups of small objects and transferring each parsed group of small objects to a respective target buffer cell 126, as described above, is continued until all groups of parsed small objects designated by the control system 30 to be deposited into the respective cassette 14 positioned beneath the buffer tray 122 have been deposited into the designated target buffer cells 126. Thereafter, the buffer tray sluice plate 130 is moved to the Open position and all the groups of small objects are transferred from (e.g., fall from) the buffer tray 122 into the corresponding cells 142 of the waiting cassette 14, i.e., into cells 142 having the same row and column number as the buffer cell 126 from which the group of small objects is being transferred. For example, with particular reference to FIGS. 2C and 6A, groups of small objects deposited in a buffer cells 126 of the buffer tray 122 having the row and column coordinates of (3,7), (7,2) and (14,5) will be transferred to the corresponding cassette cells 142 of the cassette 14 having row and column coordinates of (3,7), (7,2) and (14,5) when the buffer tray sluice plate 130 is moved to the Open position. Accordingly, the conveyor track 18, as controlled by the control system 30, precisely positions each respective cassette 14 under the buffer tray 122 of each respective filling station 26 such that the parsed groups of small object from the respective filling station 26 are accurately deposited into the designated/specified cells 142 of each respective cassette 14 as each cassette travels along the conveyor track 18.

It should be noted that during the operation described above, the distribution subsystem 42 is operating the third queuing stages 134 to sequentially receive (e.g., according to any pattern or sequence stipulated by the cassette filling code) parsed groups from the respective second queuing stages 90 of each of the respective counting and parsing subsystems 46 of the respective filling station 24 and depositing each group of small objects into a respective designated buffer cells of the buffer tray, based on mapping data utilized during execution of the cassette filling code. Additionally, in doing this, the distribution subsystem 42 can operate such that each of the third queuing stages 134 receives a group of small objects from separate second queuing stages 90 of separate counting and parsing subsystems 46, whereafter the respective groups of small objects are transferred from the respective third queuing stages 134 into respective designated buffer cells 126, as described above.

Figure 9:
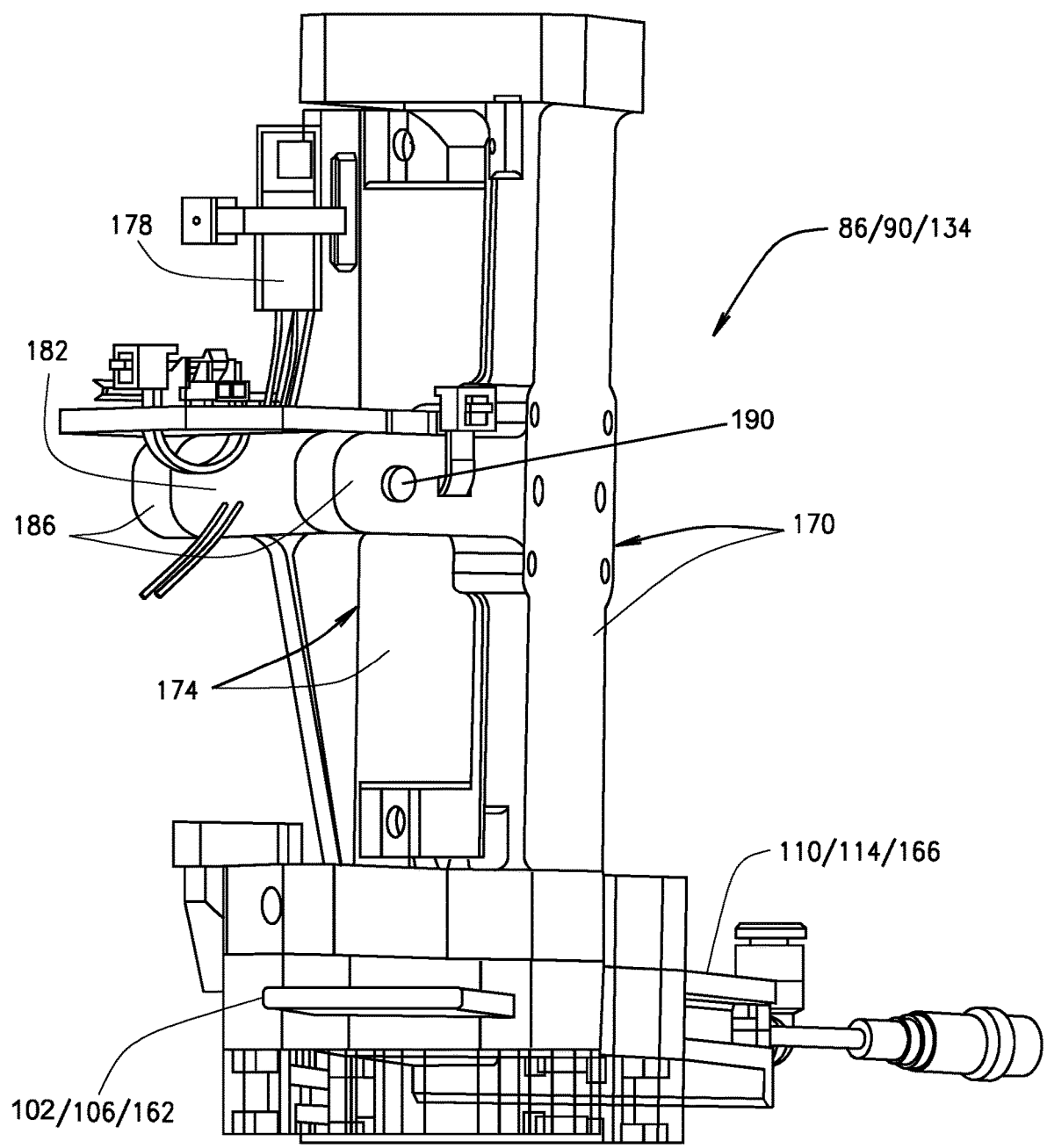
FIG. 9 is an isometric view of an exemplary queuing stage of the small object queuing assembly shown in FIG. 4 and the transport and small object deposition assembly shown in FIG. 8, in accordance with various embodiments of the present disclosure.

Referring now to FIG. 9, in various embodiments, in order to prevent small objects from jamming, lodging or binding within the respective interior chambers of one or more of the first, second and third queuing stages 86, 90 and 134, one or more of the first, second and third queuing stages 86, 90 and 134 can comprise one or more stationary or fixed walls 170 and one or more vibratory walls 174. For example, as illustrated in FIG. 9, in various embodiments, one or more of the first, second and third queuing stages 86, 90 and 134 comprises two connected or integrally formed fixed walls 170 and two connected or integrally formed vibratory walls 174 that are adjacent the fixed walls 170 such that the four walls 170/174 define the respective interior chambers. In such embodiments, each first, second and third queuing stages 86, 90 and 134 additionally comprises a vibratory motor 178 structured and operable to vibrate, move and/or shake the vibratory walls 174 relative to the fixed walls 170. For example, in various embodiments, the vibratory walls 174 include a tongue 182 that is pivotally connected to the fixed walls 170 via opposing arms 186 extending from the fixed walls 170 such that the vibratory walls 174 can pivot about a pivot pin 190 connecting the tongue 182 to the arms 186. In such embodiments, substantially simultaneously with moving the respective first, second and third sluice gates 102, 106 and 162 to the Open position, as described above, the control system 30 activates the respective vibratory motor 178 whereby the motor 178 vibrates, causing the vibratory walls 174 to vibrate, move and/or shake. The vibrating, moving and/or shaking of the vibratory walls 174 dislodges any small objects that can be jammed, lodged or bound within the respective interior chamber allowing the small object to be transferred from the respective first, second and third queuing stages 86, 90 and 134, as described above.

Figure 10:
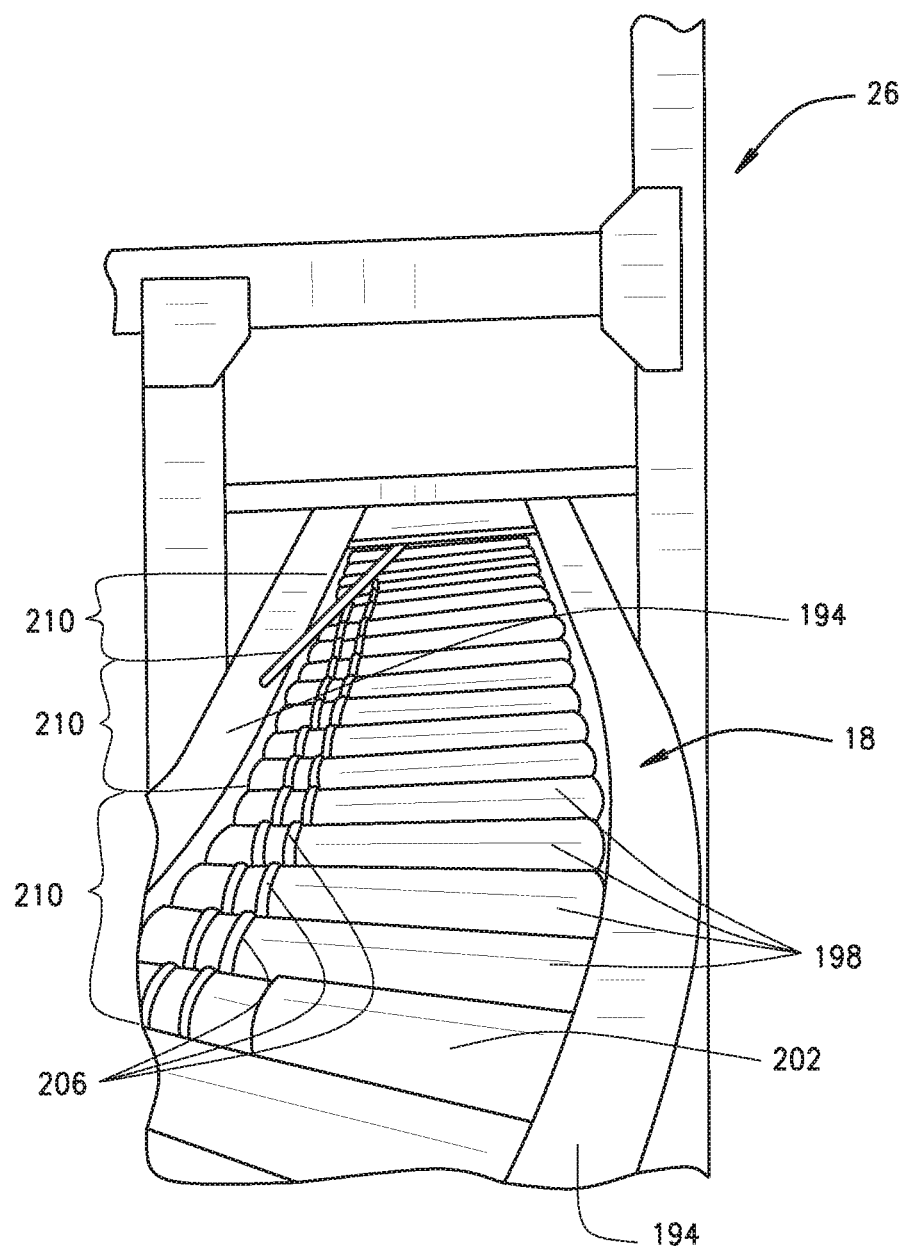
FIG. 10 is a top view of a portion of an automated conveyor track extending through a filling station of the system shown in FIG. 1, in accordance with various embodiments of the present disclosure.
Figure 11:
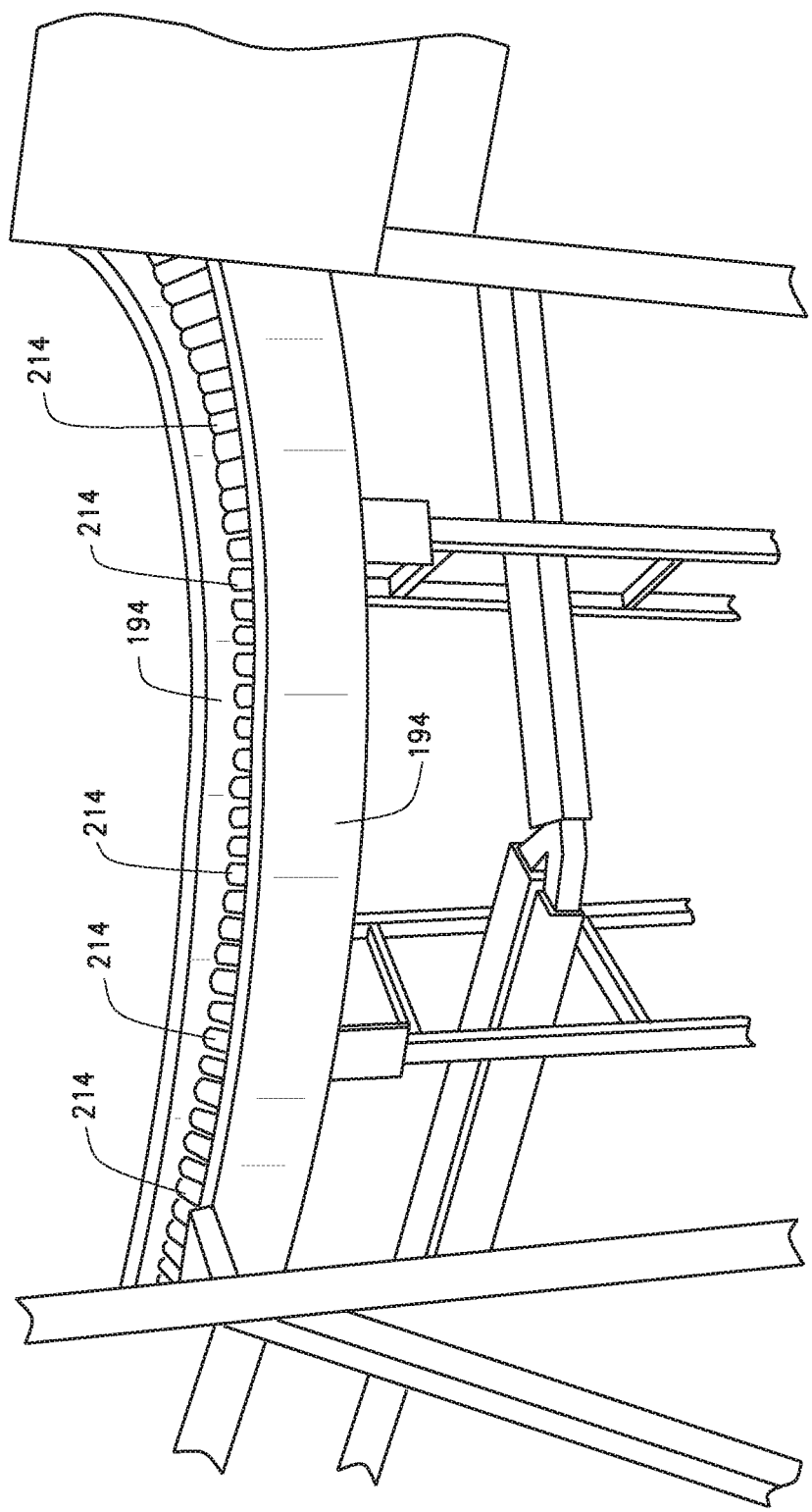
FIG. 11 is an isometric view of a portion of the automated conveyor track of the system shown in FIG. 1, in accordance with various embodiments of the present disclosure.

Referring now to FIGS. 1, 10 and 11, as described above, the automated conveyor system 18 (e.g., conveyor track 18) is structured and operable to transport the cassette(s) 14 from the loading location 34, through the one or more filling stations 26 where each cassette 14 receives the groups of small objects as described above, and then to the unloading location 38 on the conveyor track 18. As described above, in various embodiments, the conveyor system 18 can be any automated conveyor system (e.g., an automated conveyor track system) structured and operable to transport the cassette(s) 14 as described above. For example, in various embodiments wherein the conveyor system 18 comprises the conveyor track 18, the conveyor track 18 can comprise a pair of opposing side rails 194 having a plurality of passive rollers 198 and a plurality of drive rollers 202 rotationally disposed between the side rails 194. Each drive roller 202 is driven, i.e., rotated, by a respective one of a plurality of roller motors (not shown) that are controlled by the controls system 30. Each of the passive rollers 198 are operatively connected to a respective one of the drive rollers 202 such that rotation of each passive roller 198 is controlled by the rotation of the respective drive roller 202, which is controlled by the control system 30. More than one passive roller 198 can be operatively connected to each drive roller 202.

The passive and drive rollers 198 and 202 can be operatively connected using any suitable connecting means, e.g., belts, chains, gears, etc. For example, in various embodiments, each drive roller 202 is operatively connected to a passive roller 198 immediately adjacent the respective drive roller 202, (i.e., the first adjacent passive roller 198) by a belt 206 (FIG. 10). The first adjacent passive roller 198 is operatively connected to a passive roller 198 immediately adjacent the first passive roller 198 (i.e., the second passive roller 198) by another belt 206. The sequence of operative connection of subsequent adjacent passive rollers 198 can continue for any desired number of passive rollers 198, e.g., 5 to 15 passive rollers 198. Each group of rollers comprising a drive roller 202 and the respectively operatively connected passive rollers 198 form a track section 210. Hence, the conveyor track 18 comprises a plurality of sequential track sections 210, each section 210 comprising one drive roller 202 and a particular number of passive rollers 198 operatively connected to the respective drive roller 202. In various embodiments, each track section 210 has length approximately equal to a length L of the cassette(s) 14. Therefore, the sections 210 of the conveyor track 18 can be operated (i.e., the rollers 198/202 rotated), as controlled by the control system 30, to advance each cassette 14 along the conveyor track 18 one track section 210 at a time. Furthermore, each section 210 can be independently operated to independently advance and/or stop each cassette 14 at any point along the conveyor track 18. Accordingly, the control system 30 can control movement of each cassette 14 independently and precisely position each cassette 14 under the buffer tray 122 of any or all the filling stations 26 disposed over the conveyor track 18.

In various embodiments, the conveyor track 18 further includes a plurality of cassette identification sensors 214, e.g., identification label readers, disposed along the length of the conveyor track 18. The sensors 214 are structured and operable to sense the location of each cassette 14 as each cassette is transported along the conveyor track 18, and to communicate with the control system 30 such that the control system 30 can monitor and track the location of each cassette 14 as each cassette 14 is transported along the conveyor track 18. The sensors 214 can be any type of sensor suitable for reading an identification label 218 disposed each respective cassette 14, each identification label 218 providing various individual data and information regarding the respective cassette 14, the different small objects deposited or to be deposited therein, a geographical destination of each respective cassette 14, and any other desired data and/or information. The identification labels 218 can be any label suitable for providing the various data and information, e.g., radio frequency identification (RFID) labels, one-dimensional (1D) barcode labels, two-dimensional (2D) barcode labels, or any other suitable identification label. Importantly, as each cassette 14 is precisely positioned under the buffer tray 122 of a designated filling station 26, as described above, the control system 30 will, via a sensor 214, read the respective identification label 218 and thereby identify the respective cassette 14. Then based on: 1) small object type and number data, and cassette cell mapping data for the respective cassette 14 stored in one or more databases and/or electronic storage of the control system 30; and 2) the particular types of small objects the respective filling station 26 is set up to parse and dispense, which is entered into and controlled by the control system 30 as described below, the respective filling station 26 will parse and deposit the stipulated groups of small objects into the stipulated cells 142 of the respective cassette 14, as controlled by the control system 30.

Figure 12:
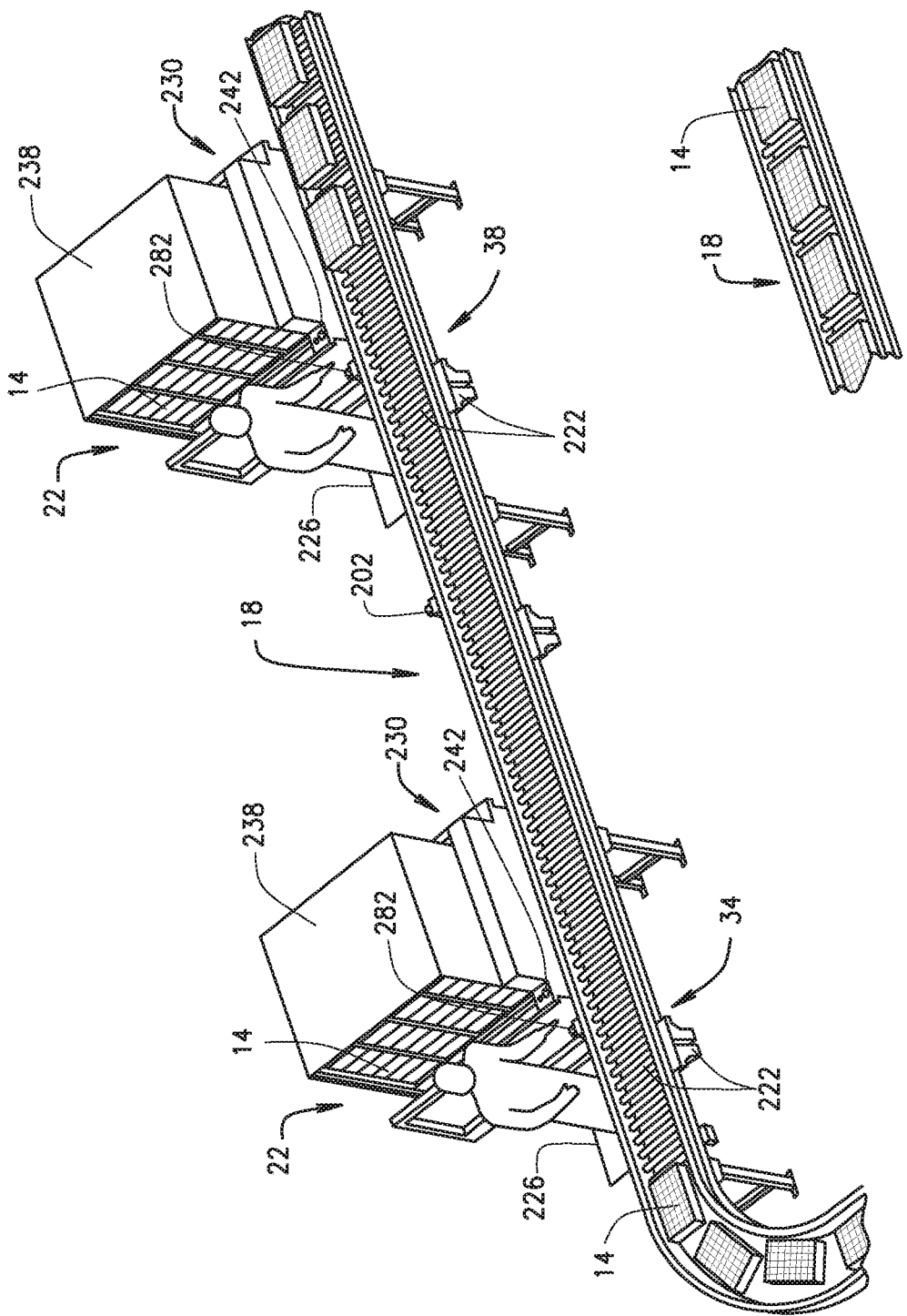
FIG. 12 is a top view of a portion of the automated conveyor track of the system shown in FIG. 1 illustrating a plurality of cassette lifts, in accordance with various embodiments of the present disclosure.

Referring now to FIGS. 1 and 12, in various embodiments the conveyor track 18 further includes a cassette lift 222 located at each of the loading and unloading locations 34 and 38 of the conveyor track 18. Operation of the cassette lift(s) 222 is controlled by an operator (human or robotic) placing cassettes 14 onto the conveyor track 18 at the loading location 34 and removing cassettes 14 from the conveyor track 18 at the unloading location 38. More particularly, a lift 222 located at the loading location 34, adjacent a first load-unload station 22, is structured and operable, as controlled by the operator, to receive cassettes 14 placed on the lift 222 by the operator and then lower the cassettes 14 onto the conveyor track 18. Conversely, a lift 222 located at the unloading location 38, adjacent a second load-unload station 22, is structured and operable, as controlled by the operator, to raise cassettes 14 off of the conveyor track 18 such that the operator can remove the cassettes 14 from the conveyor track 18. The lift(s) 222 can be controlled by any mechanism or device suitable for operation by the operator to activate (e.g., raise) the respective lift 222 and deactivate (e.g., lower) the respective life 222, e.g., a button, switch, pedal, lever, crank, etc. For example, in various embodiments, each cassette lift 222 is communicatively connected (wired or wirelessly) to a lift control pressure pad 226 of the respective load-unload station 22. In such embodiments, the operator can actuate (e.g., step onto) the pressure pad 226 to activate (e.g., raise) the respective lift 222, and then de-actuate (e.g., step off) of the pressure pad 226 to deactivate (e.g., lower) the respective lift 222.

Figure 13:
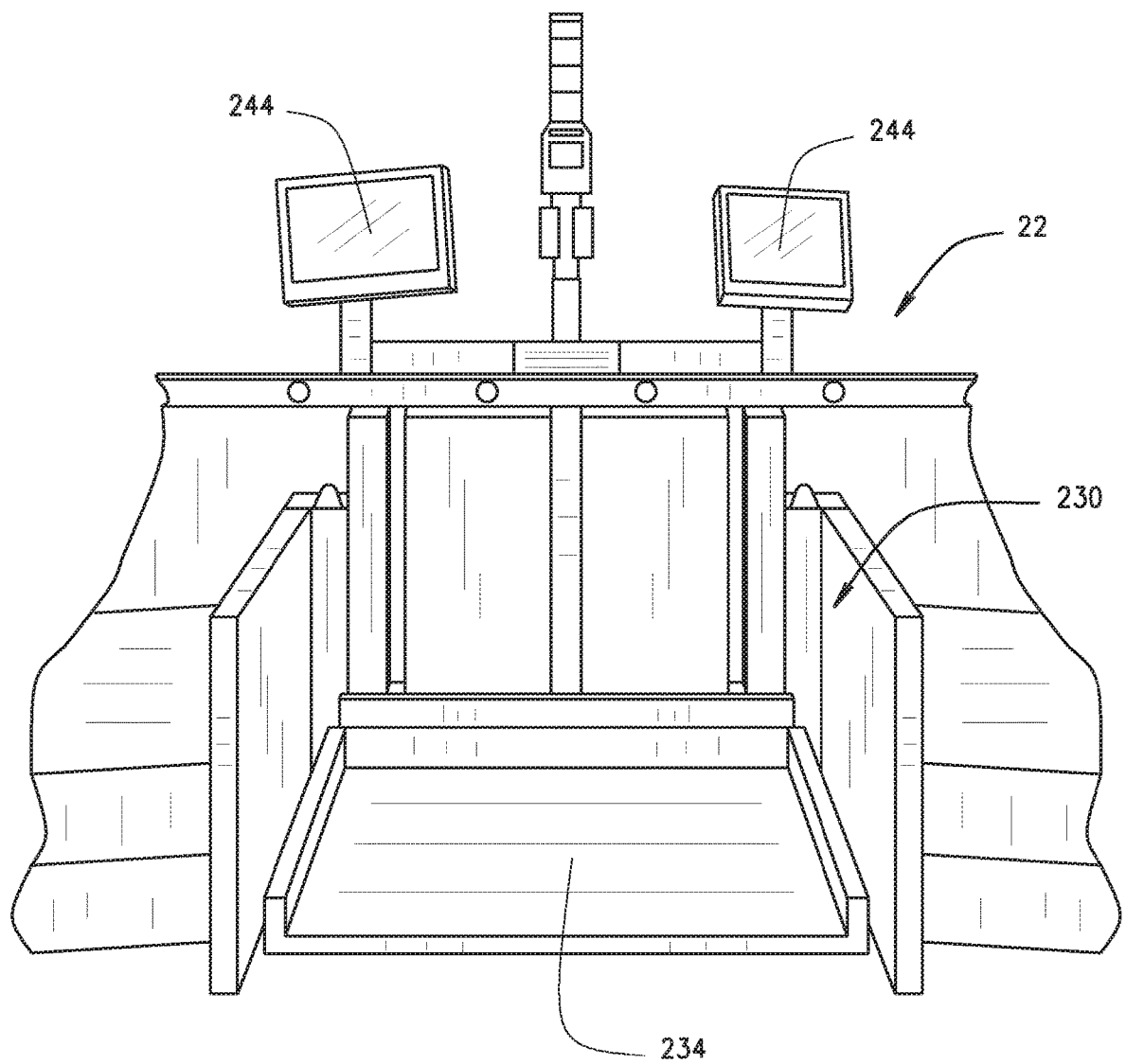
FIG. 13 is front view of a load-unload station of the system shown in FIG. 1, in accordance with various embodiments of the present disclosure.

Referring now to FIGS. 1, 12 and 13, in various embodiments, each load-unload station 22 additionally includes a cassette crate lift 230 that is structured and operable to raise and lower a cassette crate 238 that is structured and operable to retain a plurality of cassettes 14. A cassette crate 238 is generally a large shipping crate suitable for transporting a plurality of the cassettes 14 from one location to another. For example, in various embodiments, each cassette crate 238 is a large wooden cube, e.g., a 4 foot by 4 foot cube, that can be opened on opposing sides and can hold and store up to 56 or more cassettes 14. Each cassette crate lift 230 is controllable by the operator (human or robotic) via a lift control 242, e.g., buttons, levers, pedals, etc., to raise and lower a cassette crate 238 such that cassettes 14 to be removed from, or placed into, the respective crate 238 can be raised or lowered to an ergonomic height of the respective operator. In various implementations, each lift 230 comprise a lift plate 234 on which the respective crate 238 is placed. The lift plate 234 is operably connected to a lift drive (not shown), e.g., and electric motor, one or more pneumatic pistons, one or more hydraulic pistons, etc., such the operator can adjust the height of the respective crate 238 to a desired height using the lift control 242. Additionally, in various embodiments, each load-unload station 22 comprises one or more graphical display monitors 244, communicatively connected (wired or wirelessly) to the control system 30. Each display 244 displays a visual graphic of a cassette fill pattern the control system 30 currently assumes a given cassette 14 should have (e.g., the approximate number of small objects in each cell 142, unfilled cells 142, etc.), thereby providing a rapid visual confirmation to the operator. For example, an operator can verify, with a quick visual scan of a given cassette 14 being removed from the conveyor track 18, that a fill pattern of the respective cassette 14 being removed matches the respective fill pattern intended by the control system 30.

Figure 14:
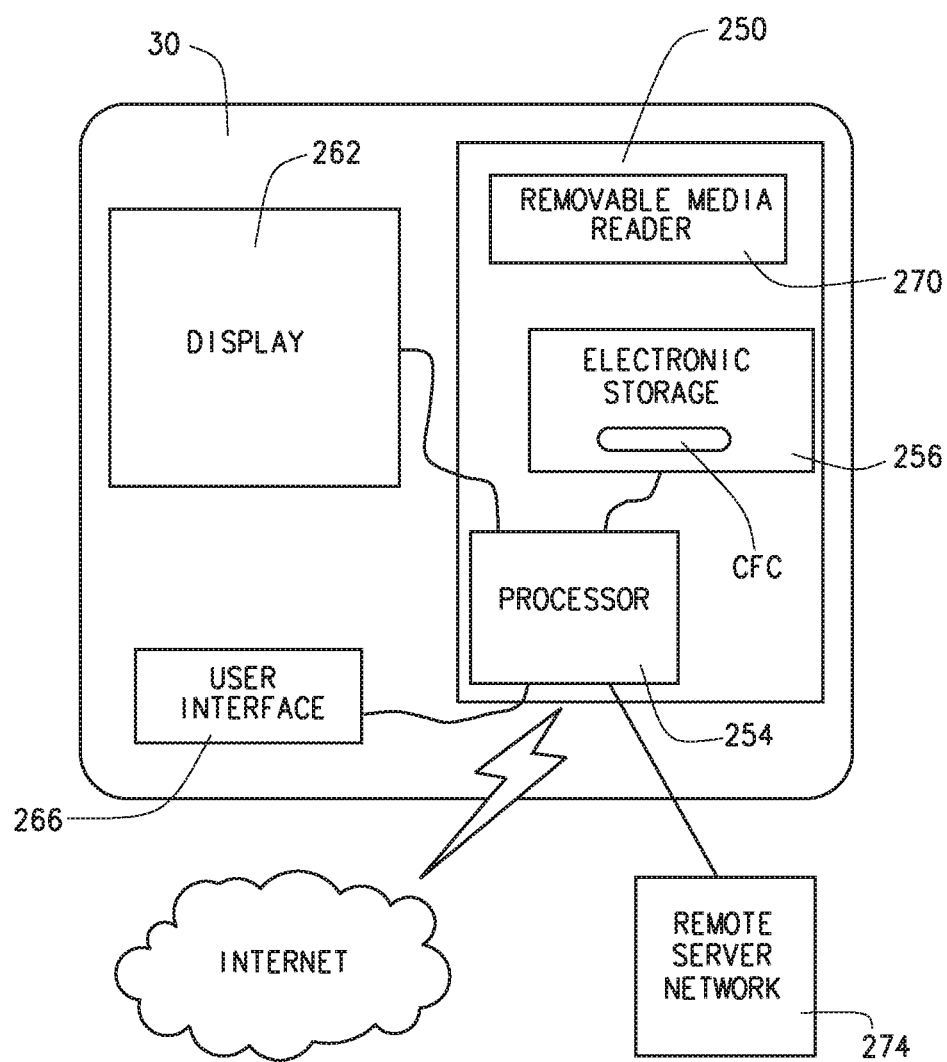
FIG. 14 is a block diagram of a central control system of the system shown in FIG. 1, in accordance with various embodiments of the present disclosure.

Referring now to FIGS. 1 and 14, as described above, the automated system 10 is controlled by the central control system 30, more particularly, by execution of the cassette filling code by a processor of the control system 30. In various embodiments, the control system 30 includes various computers and electrical modules or panels that can be located in various locations of the system 10, e.g., included in each filling station 26, included in the conveyor track 18, and included in a stand-alone console 246. More particularly, in various embodiments, the control system 30 is a computer based system that generally includes one or more computers 250 that each includes at least one processor 254 suitable to execute at least a portion of the cassette filling code (CFC) to control all automated functions and operations of the system 10, as described herein. Each computer 250 additionally includes at least one electronic storage device 258 that comprises a computer readable medium, such as a hard drive or any other electronic data storage device for storing such things as the cassette filling code or at least portions thereof, algorithms and digital information, data, look-up tables, spreadsheets and databases, etc. Furthermore, the control system 30 includes at least one display 262 for displaying such things as information, data and/or graphical representations, and at least one user interface device 266, such as a keyboard, mouse, stylus, and/or an interactive touch-screen on the display 266. In various embodiments, each computer 250 can include a removable media reader 270 for reading information and data from and/or writing information and data to removable electronic storage media such as floppy disks, compact disks, DVD disks, zip disks, flash drives or any other computer readable removable and portable electronic storage media. In various embodiments the removable media reader 270 can be an I/O port of the respective computer 250 utilized to read external or peripheral memory devices such as flash drives or external hard drives.

In various embodiments, the control system 30, e.g., one or more of the computers 250, can be communicatively connectable to one or more remote system or server network 274, e.g., a local area network (LAN) or other system operated independently of the system 10, via a wired or wireless link. For example, the control system 30 can communicate with a remote server network 274 to upload and/or download data, information, algorithms, software programs, and/or receive operational commands. Or, alternatively, the control system 30 can be in real time communication with one or more different systems operating elsewhere, e.g., seed and/or crop treatment and analytic systems such as that described in PCT application number PCT/US2015/045301, titled Apparatus And Methods For In-Field Data Collection And Sampling, filed Aug. 14, 2015, and incorporated herein by reference in its entirety. In such instances, during execution of the cassette filling code (as described above), the control system 30 can make real time, 'on-the-fly' changes, alterations and/or variations to any process, procedure, function, operation, parameter, data, etc., utilized, executed and/or implemented by the system 10 (as described above), based on information, data, coordinates, instructions, etc., received from one or more such different systems. Additionally, in various embodiments, the control system 30 can be structured and operable to access the Internet to upload and/or download data, information, algorithms, software programs, etc., to and from Internet sites and network servers.

In various embodiments, the cassette filling code is top-level system control software that not only controls the discrete hardware functionality of the system 30, but also prompts the operators (human or robotic) as to which cassette(s) 14 to load for the most efficient filling of the cassette(s) 14. In order to maximize throughput of the system 30, it is important that the operators load cassette(s) onto the conveyor track 18 in the most efficient order. To enable this, the cassette filling code interfaces with an inventory monitoring system that contains information regarding the types and quantities of small objects, e.g., different types and quantities of hybrid seed, stored in a storage area near the system 30 to determine which types of small objects are available. Since all small objects needed to fill every cassette 14 can not be available at the start of a filling season, it is important that the system 30 tracks and monitors which types and quantity of small objects are available. With this information, the control system 30 can determine which small objects should be loaded into each of the filling stations 26 and which cassette(s) 14 should be loaded onto the conveyor track 18. In various embodiments, the control system 30 communicates with the inventory monitoring system to provide a list of which types and quantities of small objects have been removed from inventory.

Figure 15:
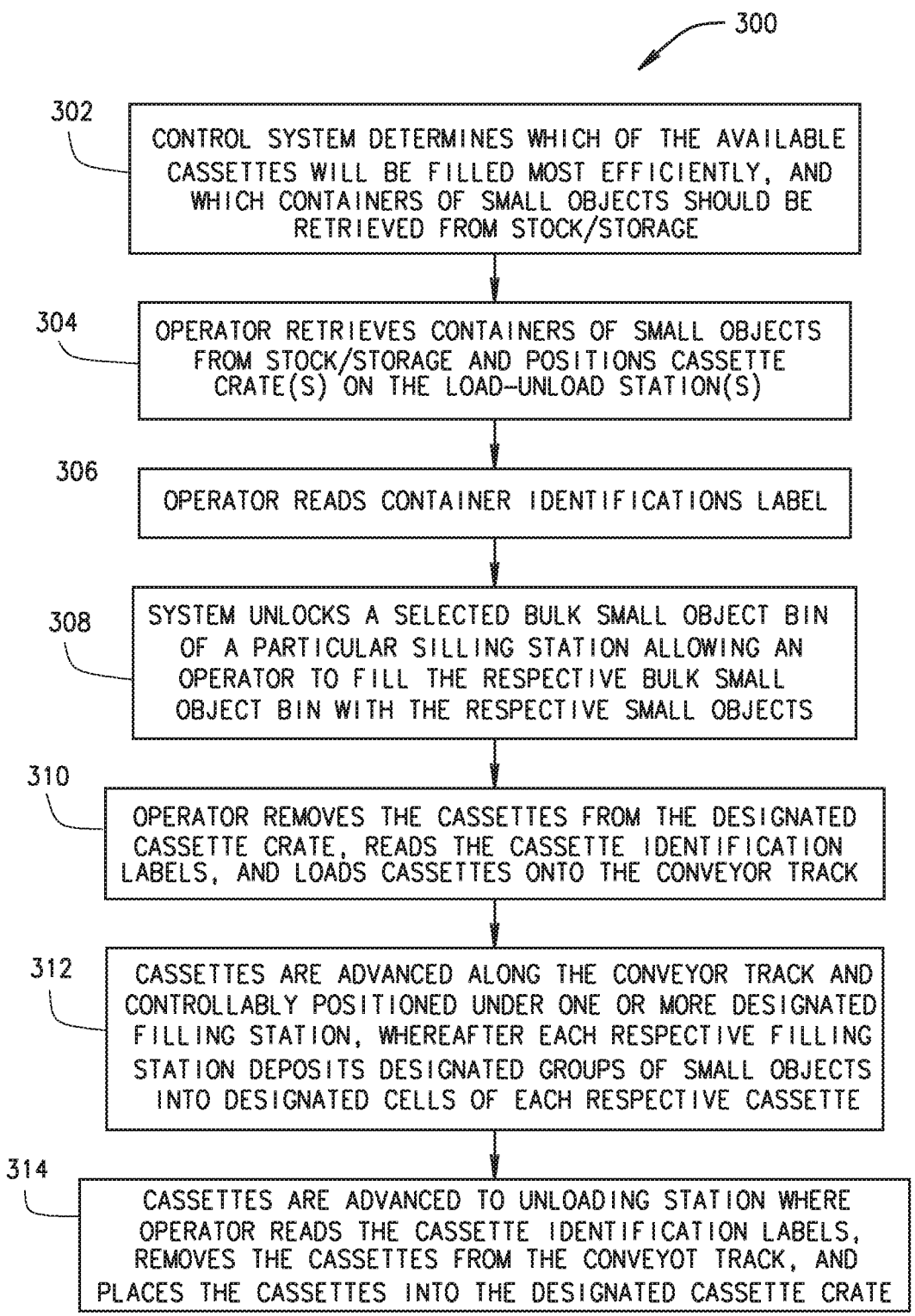
FIG. 15 is a flow chart illustrating a sequence of events during operation of the system shown in FIG. 1, in accordance with various embodiments of the present disclosure.

Referring now to FIGS. 1 through 15, in operation, FIG. 15 provides a flow chart 300 illustrating a sequence of events during operation of the small object parsing and cassette filling system 10, in accordance with various embodiments of the present disclosure. Initially, based on the known inventory of types and quantities of small objects (e.g., different types and quantities hybrid seed) available for use, the known available cassettes 14 needing to be filled, and the geographic destination of each respective cassette 14 to be filled, the system 30 determines which of the available cassettes 14 will be most efficiently filled by the system 10 and which containers (e.g., bags) of small objects should be retrieved from stock/storage, as indicated at 302. The control system 30 will provide this information to an operator, e.g., by displaying this information on a display 262 of the control system 30 and/or providing a printed copy of the information. Armed with this information, an operator (human or robotic) will retrieve the indicated containers of small objects from stock and will position one or more cassette crates 238 retaining one or more of the indicated cassettes 14 on the lift plate(s) 234 of one or more of the load-unload stations 22 positioned adjacent one or more loading locations 34 of the conveyor track 18, as indicated at 304.

Subsequently, an operator places each container of retrieved small objects adjacent particular filling stations 26 as determined and indicated by the control system 30. Thereafter, an operator reads a container identification label of a respective container using a container identification label reader 278 (FIG. 3) of the respective filling station 26 stipulated by the control system 30 to parse groups of small objects from the respective container, as indicated at 306. The container identification labels and reader 278 can be any label and associated reader suitable for providing and reading various data and information regarding the small objects contained in the respective container, e.g., radio frequency identification (RFID) labels and reader, one-dimensional (1D) barcode labels and reader, two-dimensional (2D) barcode labels and reader, or any other suitable identification label and reader. Once the container identification label has been read, the control system 30 determines if the respective container and small objects therein are to be counted and parsed by the respective filling station 26. If so, the control system 30 unlocks a selected one of the bulk small object bin lockable lids 54, designated by the control system 30, such that the operator can deposit a quantity of the small objects from the respective container into the unlocked bulk small object bin 50, as indicated at 308. This process is repeated until small objects from each of the containers retrieved from stock/storage have been deposited into the designated bulk small object bins 50 of the designated filling stations 26.

Prior to, simultaneously with, or subsequent to the operator filling the bulk small object bins 50, as described above, an operator at the 'loading' load-unload station(s) 22 where the cassette crate(s) 238 has/have been positioned begins loading the cassettes 14 therein onto the conveyor track 18, as indicated 310. To load a cassette 14 onto the conveyor track 18 the operator: 1) reads the cassette identification label 218 using a suitable cassette identification label reader 282 of the conveyor track 18 located at the respective loading location 34 of the conveyor track 18 (FIG. 12); 2) removes the respective cassette 14 from the crate 238; 3) actuates the cassette lift to raise the cassette lift 222 located at the respective loading location 34 of the conveyor track 18 (e.g., steps on the respective pressure pad 226); 4) places the cassette 14 onto the raised lift 222; and 5) de-actuates the lift 222 to lower the respective cassette 14 onto the conveyor track 18 (e.g., steps off the pressure pad 226), whereafter the cassette 14 is advanced along the conveyor track 18 by the rollers 198 and 202, as described above. The sequence of reading the cassette identification labels 218, removing the cassettes 14 from the cassette crate 238, actuating the lift 222, and placing the cassette onto the lift 222 is only an exemplary sequence and is not limiting, rather these steps/functions can be performed by the operator in any desired order and remain within the scope of the present disclosure.

As the cassettes 14 are loaded onto the conveyor track 18, they are controllably advanced from one track section 210 to the next such that each cassette 14 is sequentially positioned under the buffer trays 122 of one or more designated filling stations 26, whereafter the designated filling stations 26 deposit groups of small objects into the designated cassette cells 142, all as controlled by the control system 30 and described above, as indicated at 312. Hence, each cassette 14 loaded onto the conveyor track 18 is controllably advanced along the track 18, one section 210 at a time, and sequentially positioned under one or more of the filling stations 26, whereafter each respective filling station 26 parses groups of small objects, as designated and controlled by the system controller 30, and deposits each parsed group of small objects into specific cells 142 of the respective cassettes 14, as designated and controlled by the system controller 30, until each cassette 14 has passed through each of the filling stations 26, receiving groups of small objects only from those filling stations 26 designated by the control system 30.

Once a cassette 14 has been advanced through each of the filling stations 26, the cassette 14 is advanced to an unloading location 38 of the conveyor track 18, where the control system 30 positions the cassette 14 over the lift 222 located at the respective unloading location 38 of the conveyor track 18, whereafter an operator unloads, i.e., removes, the cassette from the conveyor track and places into a designated cassette crate 238, as indicated at 314. To unload, i.e., remove, a cassette 14 from the conveyor track 18 the operator: 1) actuated the cassette lift 22 to raise the cassette lift 222 located at the respective unloading location 38 of the conveyor track 18 (e.g., steps on the respective pressure pad 226) and thereby raise the cassette 14 off the roller 198 and 202 of the conveyor track 18; 2) reads the cassette identification label 218 using a suitable cassette identification label reader 282 located at the respective unloading location 38 of the conveyor track 18 so the control system 30 can track/monitor the location of the respective cassette and what groups of small objects have been deposited therein; 3) removes the respective cassette 14 from the raised lift 222; 4) de-actuates the lift 222 to lower the lift 222 (e.g., steps off the pressure pad 226); and 5) places the respective cassette 14 into the designated cassette crate 238. The sequence of actuating the lift 222, reading the cassette identification labels 218, removing the cassettes 14 from the lift 222, and placing the cassette into the designated crate 238 is only an exemplary sequence and is not limiting, rather these steps/functions can be performed by the operator in any desired order and remain within the scope of the present disclosure.

After all the selected cassettes 14 designated to receive a particular type of small object, e.g., a particular hybrid of seed, have received the designated groups of the particular type of small objects, that type of small object can be purged from the respective filling station 26 via a purging conduit 286 (FIG. 4). In various embodiments, the purging conduit 286 is connected at an upper end to an evacuation port (not shown) of the upper small object bin 66 and at a lower end to the bulk small object bin 50 of the respective counting and parsing subsystem 46 of the respective filling station 26. To purge the small objects the control system 30 opens the respective evacuation port, thereby allowing the force of gravity to cause all the small objects within the respective upper small object bin 66 to fall through the purging conduit into the respective bulk small object bin 50. Additionally, any small objects remaining within the singulator and counter 74, or the first, second or third queuing stages 86, 90 or 134 can be cycled through the respective queuing stages, as described above, and deposited, via the transport and small object deposition assembly 118, into a purge pan 290 (FIG. 6) of the small object distribution subsystem 42. Thereafter, subsequent types of small objects can be parsed and deposited into the cassettes 14 that were not removed from the conveyor track 18 or cassettes 14 that are subsequently loaded onto the conveyor track 18, as described above.

As described above, the cassette processing stations 26 can be structured and operable to perform many different operations, procedures and analysis on the cassettes 14 and or small objects deposited therein, other than as a cassette filling stations. For example, it is envisioned that, in addition to or instead of, the cassette processing stations 26 parsing groups of small objects, such as seeds, from a plurality of bulk quantities of different types of small objects and depositing the parsed groups of small objects into cells 142 of a small object cassette 14, the cassette processing stations 26 can be structured and operable to apply a coating or treatment to any, all or selected groups of small objects and/or cells 142 prior to and/or subsequent to the small objects being deposited in cassettes 14. For example, the system 10 can be structured and operable to apply microbial and/or chemical treatments in any form, including liquids, gasses, and semi-solids, powders, etc., to any, all or selected groups of small objects and/or cells 126 and/or 142 prior to and/or subsequent to the small objects being deposited in cassettes 14. Additionally, the treatment can include such things a chemicals to clean the cells 126 and/or 142, or autoclavable components, or lubricants, etc.

Still further, it is envisioned that in various embodiments, in addition to or instead of, the cassette processing stations 26 parsing groups of small objects, such as seeds, from a plurality of bulk quantities of different types of small objects and depositing the parsed groups of small objects into cells 142 of a small object cassette 14, the cassette processing stations 26 can be structured and operable to perform various analytic procedures on the small objects to analyze and/or assay and/or determine such things as oil content of the small objects deposited in one or more cell 142, the volume of the small objects deposited in one or more cell 142, the weight of the small objects deposited in one or more cell 142, the size and/or shape of small objects deposited in one or more cell 142. Such embodiments of the system 10 can include analytic and measurement devices such as lasers, optical imaging devices, X-ray imaging devices, magnetic imaging devices, microwave imaging devices, IR imaging devices, meters, scales, etc. that are capable of collecting image data and other data regarding any desired metric if the respective small objects.

Still further yet, it is envisioned that, in various embodiments, the system 10 can include: 1) one or more cassette processing station 26 that is structured and operable to parse groups of small objects, from a plurality of bulk quantities of different types of small objects and depositing the parsed groups of small objects into cells 142 of a small object cassette 14 (as described above); 2) one or more cassette processing station 26 that is structure and operable to apply a coating or treatment to any, all or selected groups of small objects and/or cells 142 prior to and/or subsequent to the small objects being deposited in cassettes 14 (as described above); and/or 3) one or more cassette processing stations 26 structured and operable to perform various analytic procedures on the small objects (as described above).

Still yet further, it is envisioned that, in various embodiments, any method of preparing and/or processing and/or sorting the small objects that are loaded into a cassette 14 can be used in conjunction with the methods described herein. For example, in various embodiments, seeds can be separated from other plant parts using any method and/or device, e.g. harvesting, shelling, threshing, ginning, etc., before and/or during and/or after being loaded into a cassette 14. Furthermore, in various instances, before and/or during and/or after a seed is loaded into a cassette 14, the seed(s) can be subjected to any number of tests, trials, or analyses known to be useful for evaluating plant performance, including any phenotyping or genotyping assay known in the art. These include, but are not limited to, any imaging, optical, chemical, or physical technique useful for distinguishing or characterizing the seed(s) (small objects) in question. For example, a user can collect data about the contents of a cassette 14 based on visible light, NMR, X-ray, MRI, microwave, or any other type or combination of electromagnetic signal. In various embodiments, it can be advantageous to test and/or sort and/or select plants based on assays that can be conducted without germinating a seed or otherwise cultivating a plant sporophyte. Common examples of seed phenotypes include size, shape, surface area, volume, mass, and/or quantity of chemicals in at least one tissue of the seed, e.g. anthocyanins, proteins, lipids, carbohydrates, etc., in the embryo, endosperm or other seed tissues. In various embodiments, the presence of at least one reporter molecule that binds to at least one specified nucleic acid or amino acid sequence that the user wishes to use to differentiate the seeds in a population is used in conjunction with the methods disclosed herein. In various embodiments, wherein the small objects are seeds, the seeds can be differentiated based on the presence or absence of particular isotopes, e.g., C12 vs. C14. In some embodiments, this detection is accomplished by the use of rapid mass spectrometry. In various embodiments, seeds can be analyzed and/or distinguished and/or sorted based on data collected using computerized (or computed) tomography, including methods such as those described in U.S. Provisional Application 62/055,861, filed Sep. 26, 2014, and PCT Application PCT/US2015/052133, filed Sep. 25, 2015, titled High Throughput Methods Of Analyzing Seed Cotton Using X-Ray Imaging. Additionally, in various embodiments, seeds can be analyzed, distinguished, and/or sorted based on oil content and/or water content, and/or their weight, such as described in U.S. Provisional Application 61/791,411, filed Mar. 15, 2013, U.S. application Ser. No. 14/206,238, filed Mar. 12, 2014, and PCT Application PCT/US/2014/025174, filed Mar. 13, 2014, titled High-Throughput Sorting Of Small Objects Via Oil And/Or Moisture Content Using Low-Field Nuclear Magnetic Resonance; and/or U.S. Provisional Application 62/051,000, filed Sep. 16, 2014, and PCT Application PCT/US2015/049344, filed Sep. 10, 2016, titled Improved Methods Of Plant Breeding Using High-Throughput Seed Sorting.

In various embodiments, tissues of the seed can also be genotyped using any method useful to the breeder. Common examples include harvesting a sample of the embryo and/or endosperm in a way that does not kill or otherwise prevent the embryo from surviving the ordeal, i.e., seed chipping. Automated examples of these methods can be found in the following list of US Applications and issued Patents. U.S. Pat. Nos. 7,502,113; 7,611,842; 7,849,632; 7,703,238; 8,312,672; 8,959,833; 7,830,516; 7,832,143; 8,245,439; 8,443,545; 8,997,398; 8,539,713; 7,941,969; 7,591,101; 8,434,259; PCT/US2013/0244321; U.S. Pat. Nos. 7,998,669; 8,028,469; 9,027,278; 7,877,926; 8,561,346; 9,003,696; 7,767,883; 8,071,845; and 8,436,225. Any other method of harvesting samples of tissues of the seed for analysis can be used for the purposes of genotyping, as well as conducting genotyping assays directly on the tissues of the seed that do not require a sample of tissue to be removed. In various embodiments, the embryo and/or endosperm remain connected to other tissues of the seed. In various embodiments, the embryo and/or endosperm is separated from other tissues of the seed (e.g. embryo rescue, embryo excision, etc.).

In any way that a tissue of the seed might be accessed, there are a wide range of methods that can be employed to genotype them. Commonly used methods include using at least one molecular marker (e.g. a single-nucleotide polymorphism, or SNP, marker) and/or at least one sequencing-based method (e.g. genotype by sequencing, or GBS) to detect the presence of certain nucleotide sequences in the embryo or endosperm of a seed. It is anticipated that other useful method of detecting, quantifying, or comparing a nucleotide sequence in a plant embryo or endosperm could be employed in conjunction with methods described herein, depending on the circumstances (e.g. species of plant, number of plants to genotype, size of breeding program, etc.). Any genotyping method that a user employs to aid in the process of selecting seeds (or embryos, or endosperms) for advancement to a next step in a breeding process could be useful with these methods.

In the same way that users of the methods disclosed herein are not limited to certain genotyping or phenotyping methods or technologies when assaying the tissues on and/or within a seed, any method or technology that aids in the determination of a genotype or phenotype of a plant or plant cells at any stage of the life cycle could be used in conjunction with the methods described herein. For example, a plant researcher can desire to actually germinate a seed from a cross and/or cultivate the plant from an embryo to some later development stage in order to complete a test useful for making selections on the plant.

It is anticipated that those of ordinary skill will appreciate that the methods disclosed herein are not limited to the type of data about a plant that are collected, or how they are collected, or how they are analyzed and that any method of scoring and/or comparing a plant or plant cell type with another could be used to make a selection. Some of the common examples of criteria used by plant researchers to evaluate germinated plants include yield (e.g. measured by the amount of harvested plant chemicals and/or tissues), disease and/or stress tolerance, robustness, germination rate (e.g. following seed chipping), cost to produce a product (e.g. "cost of goods"), propensity to produce haploid offspring (induction), the propensity of cells of haploid offspring to have their chromosome number doubled (i.e. chromosome doubling), presence or absence of certain nucleotide sequences (e.g. molecular genotyping/phenotyping), amount of seed set, amount of pollen production, and any other trait or characteristic a researcher desires to increase, decrease, or maintain the frequency of in a population of plants.

Furthermore, the identity of the small objects can be electronically assigned and/or maintained and/or determined in conjunction with these methods using any technique or device the user desires to employ, including computer-based methods, e.g. using bar codes and/or radio-frequency identification to track the small objects before and/or during and/or after being loaded into a cassette.

Furthermore, although the small object counting and parsing subsystems 46 have been described to count the small objects to be deposited in the various object queueing stations 86/90/134, it is envisioned that, in various embodiments, the small object counting and parsing subsystems 46 can be structured and operable to quantify and dispense the small objects into the object queueing stations 86/90/134 based on any other desired metric such as weight, oil content, size, shape, volume, etc.

Even further, although the vibrator walls 174 have been described above with regard to use in the object queueing stages 86/90/134, it is envisioned that, in various embodiments, the vibrator walls 174 and the likes thereof can be implemented anywhere within any one or more of the cassette processing stations where the small objects can get bridged, lodged, jammed, stuck or bound between the bulk small object bins 50 and the cassette cells 142. Additionally, it should be noted that in arriving at the embodiments of the vibrator walls 174 described above, various tests and iterations were attempted and performed. For example, it was attempted to implement a vibratory motor to vibrate the sluice gates 94, 98 and 102. However, this did not adequately transfer vibration through the entire column height of the object queueing stages 86/90/134 to prevent bridging, and when bridging did occur, the vibration was insufficient to break up the bridge. Another attempt involved striking the object queueing stages 86/90/134 with a mass to unsettle bridge formation in the seed volume. But, tests revealed that the mass required to prevent and/or break up bridging so great that it added an unacceptable amount of weight to the object queueing stages 86/90/134. A further attempt included increasing the cross sectional area of the object queueing stages 86/90/134, which was accomplished by splitting the respective queueing station into two parts along the diagonal of the square cross section. One half was rigidly mounted to the system, while the other half was moved via a pneumatic actuator. Test revealed that this solution can work, however, there is a concern that further modifications are needed to achieve a desired rate of efficacy.

The final solution of implementing the vibrator walls 174, as described above, to solve a bridging problem employed a vibratory motor, and the concept of splitting the respective queueing stage 86/90/134 into two parts, and instead connecting the vibratory motor to the sluice gates 94, 98 and 102, the vibratory motor was connected to one half (e.g., one of two longitudinal walls) of the respective queueing stage 86/90/134. The vibratory motor is mounted to insure the motor's rotation axis is 90° to the pivot axis (e.g., the pivot pin 190), so that each rotation of the motor induces a corresponding shift in location of the pivoting queue half. In essence, each rotation of the motor changes the cross sectional area of the queue. Additionally, the pivot axis is located away from the queue interior cross section to exaggerate the rocking movement and insure the entire column height has a change in cross section (if the pivot point is too close, there would be very little movement nearest the pivot). The vibratory motor was specified empirically to provide the most desirable movement impulse into the mechanism. Smaller motors did not provide sufficient vibration, and larger motors vibrated the entire queue, not just the walls 174 of the queueing stage, which will likely lead to loose parts, unnecessary wear and tear, and/or premature fatigue failure. Finally, the vibratory motor, versus pneumatic actuator, provided two main benefits: 1) the vibratory motor provides many more (e.g., hundreds more) movement cycles per seed transfer than the pneumatic actuator, thus greatly increasing the probability that a small object bridge will be cleared on a movement cycle, and 2) the vibratory motor is small and weighs less than a pneumatic actuator.

The following are definitions of words and/or phrases that are used herein. As used herein, a microbe will be understood to be a microorganism, i.e. a microscopic living organism, which can be single celled or multicellular. Microorganisms are very diverse and include all the bacteria, archea, protozoa, fungi, and algae, especially cells of plant pathogens and/or plant symbiots. Certain animals are also considered microbes, e.g. rotifers. In various embodiments, a microbe can be any of several different microscopic stages of a plant or animal. Microbes also include viruses, viroids, and prions, especially those which are pathogens or symbiots to crop plants. As used herein the term plant refers to a whole plant, any part thereof, or a cell or tissue culture derived from a plant, comprising any of: whole plants, plant components or organs (e.g., leaves, stems, roots, etc.,), plant tissues, seeds, plant cells, and/or progeny of the same. A plant cell is a biological cell of a plant, taken from a plant or derived through culture from a cell taken from a plant. As used herein the term fungus refers to a whole fungus, any part thereof, or a cell or tissue culture derived from a fungus, comprising any of: whole fungus, fungus components or organs, fungal tissues, spores, fungal cells, including cells of hyphae and/or cells of mycelium, and/or progeny of the same. A fungus cell is a biological cell of a fungus, taken from a fungus or derived through culture from a cell taken from a fungus.

Further, as used herein the phrase population of plants or plant population means a set comprising any number, including one, of individuals, objects, or data from which samples are taken for evaluation, e.g. estimating QTL effects and/or disease tolerance. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but can also derive from two or more crosses between the same or different parents. Although a population of plants can comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population.

Additionally, as used herein the term tolerance or improved tolerance in a plant to disease conditions will be understood to mean an indication that the plant is less affected by disease conditions with respect to yield, survivability and/or other relevant agronomic measures, compared to a less tolerant, more "susceptible" plant. Tolerance is a relative term, indicating that a "tolerant" plant survives and/or produces better yields in disease conditions compared to a different (less tolerant) plant (e.g., a different corn line strain) grown in similar disease conditions. As used in the art, disease "tolerance" is sometimes used interchangeably with disease "resistance." One of skilled in the art will appreciate that plant tolerance to disease conditions varies widely, and can represent a spectrum of more-tolerant or less-tolerant phenotypes. However, by simple observation, one of skill in the art can generally determine the relative tolerance or susceptibility of different plants, plant lines or plant families under disease conditions, and furthermore, will also recognize the phenotypic gradations of "tolerant."

Still further, as used herein, crop or plant performance is a metric of how well a crop plant grows under a set of environmental conditions and cultivation practices. Crop/plant performance can be measured by any metric a user associates with a crop's productivity (e.g. yield), appearance and/or robustness (e.g. color, morphology, height, biomass, maturation rate), product quality (e.g. fiber lint percent, fiber quality, seed protein content, seed carbohydrate content, etc.), cost of goods sold (e.g. the cost of creating a seed, plant, or plant product in a commercial, research, or industrial setting) and/or a plant's tolerance to disease (e.g. a response associated with deliberate or spontaneous infection by a pathogen) and/or environmental stress (e.g. drought, flooding, low nitrogen or other soil nutrients, wind, hail, temperature, day length, etc.). Crop/plant performance can also be measured by determining a crop's commercial value and/or by determining the likelihood that a particular inbred, hybrid, or variety will become a commercial product, and/or by determining the likelihood that the offspring of an inbred, hybrid, or variety will become a commercial product. Crop/plant performance can be a quantity (e.g. the volume or weight of seed or other plant product measured in liters or grams) or some other metric assigned to some aspect of a plant that can be represented on a scale (e.g. assigning a 1-10 value to a plant based on its disease tolerance).

The methods disclosed herein can be employed on any fruit, vegetable, grass, tree, or ornamental crop, including, but not limited to, maize (*Zea mays*), soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including *indica* and *japonica* varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*), members of the genus *Brassica*, including broccoli, cabbage, cauliflower, canola, and rapeseed, carrot, Chinese cabbage, cucumber, dry bean, eggplant, fennel, garden beans, gourd, leek, lettuce, melon, okra, onion, pea, pepper, pumpkin, radish, spinach, squash, sweet corn, tomato, watermelon, honeymelon, cantaloupe and other melons, banana, castorbean, coconut, coffee, cucumber, Poplar, Southern pine, Radiata pine, Douglas Fir, Eucalyptus, apple, and other tree species, orange, grapefruit, lemon, lime and other citrus, clover, linseed, olive, palm, Capsicum, Piper, and Pimenta peppers, sugarbeet, sunflower, sweetgum, tea, tobacco, and other fruit, vegetable, tuber, and root crops.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A high throughput system for sorting a plurality of different small object types into a plurality of cells of at least one small object cassette, said system comprising:
   the at least one small object cassette comprising a plurality of inter-connected small object cells integrally formed in the at least one small object cassette, the inter-connected, integrally formed small object cells structured to retain small objects;
   an automated closed-circuit conveyor system comprising a plurality of sequential independently controlled track sections, the conveyor system structured and operable to transport the cassette(s) from a cassette loading station around the closed-circuit conveyor system, through at least one cassette processing station, and to a cassette unloading station;
   the at least one cassette processing station accessible by the conveyor system and structured and operable to deposit one of a plurality of groups of the small objects into selected ones of the inter-connected small object cells integrally formed in the at least one small object cassette; and
   a central control system comprising a computer-based controller communicatively connected to at least the conveyor system and each cassette processing station, the central control system structured and operable to control operations of each independently controlled track section of the conveyor system and each cassette processing station.

2. The system of claim 1, wherein each processing station comprises:
   at least one small object counting and parsing subsystem structured and operable to parse the plurality of groups of small objects from a bulk quantity of the small objects, each group of small objects comprising a respective number of small objects stipulated by the central control system; and
   a small object distribution subsystem structured and operable to receive each parsed group of small objects and deposit each parsed group of small objects into a respective one of the small object cells of a respective one of the cassette(s) stipulated by the central control system as the respective cassette is positioned adjacent the small object distribution subsystem via the conveyor system.

3. The system of claim 2, wherein each small object counting and parsing subsystem comprises:
   a bulk small object bin structured and operable to retain the bulk quantity of small objects of a selected type;
   an upper small object bin structured and operable to retain small objects received from the bulk small object bin;
   a decelerator connected to the bulk small object bin by a vacuum conduit structured and operable to transport a plurality of small objects from the bulk small object bin to the decelerator, the decelerator additionally connected to the upper small object bin, wherein the decelerator is structured and operable to decelerate a speed of the small object being transported from the bulk small object bin and deposit them into the upper small object bin;

a small object singulator and counter connected to the upper small object bin, the small object singulator and counter structured and operable to extract small objects from the upper small object bin, count the small objects and parse the small objects into the groups of small objects wherein each group of small objects comprises the respective number of small objects stipulated by the central control system; and a small object queuing assembly structured and operable to receive the groups of small objects from the small object singulator and counter and deposit each group of small objects into the small object distribution subsystem.

4. The system of claim 3, wherein the small object queuing assembly comprises:
   a first queuing stage fluidly connected to the small object singulator and counter and structured and operable to receive and temporarily retain each group of small objects from the small object singulator and counter; and
   a second queuing stage fluidly connected to the first queuing stage and structured and operable to receive and temporarily retain each group of small objects from the first queuing stage.

5. The system of claim 4, wherein the small object distribution subsystem comprises:
   a multi-cell buffer tray comprising a plurality of small object buffer cells;
   a small object transport and deposition assembly structured and operable to deposit groups of small objects received from the small object queuing assembly into selected small object buffer cells; and
   a sluice tray that is movable between a Closed position and an Open position, wherein when in the Closed position the sluice tray covers the bottom of buffer tray such that groups of small objects deposited in the small object buffer cells are retained within the small object buffer cells, and when in the Open position the sluice tray uncovers the bottom of the buffer tray such that the groups of small objects deposited in the buffer cells are allowed to fall into corresponding small object cells of a small object cassette positioned under the buffer tray via the automated conveyor system.

6. The system of claim 5, wherein the small object deposition assembly comprises at least one third queuing stage mounted to an X-Y transport, the third queuing stage (s) structured and operable to receive and temporarily retain each group of small objects from the second queuing stage and deposit each group of small objects into a respective the selected small object buffer cell, the X-Y transport structured and operable to position the third queuing stage(s) under the second queuing stage and then subsequently over the respective small object buffer cell.

7. The system of claim 6, wherein at least one of:
   the first queuing stage comprises a first stage vibratory wall structured and operable to vibrate to prevent small objects from becoming lodged within the first queuing stage;
   the second queuing stage comprises a second stage vibratory wall structured and operable to vibrate to prevent small objects from becoming lodged within the second queuing stage; and
   the third small object queuing stage comprises a third stage vibratory wall structured and operable to vibrate to prevent small objects from becoming lodged within the third queuing stage.

8. A high throughput system for sorting a plurality of different small object types into a plurality of cells of at least one small object cassette, said system comprising:
   the at least one small object cassette comprising a plurality of inter-connected small object cells integrally formed in the at least one small object cassette, the inter-connected, integrally formed small object cells structured to retain small objects;
   an automated closed-circuit conveyor track comprising a plurality of sequential independently controlled track sections, the conveyor system structured and operable to transport the cassette(s) from a cassette loading location around the closed-circuit conveyor track, through at least one cassette processing station, and to a cassette unloading location;
   the at least one cassette processing station disposed over the conveyor track such that the conveyor track extends through each cassette processing station and under a small object distribution subsystem of each respective cassette processing station, wherein the at least one cassette processing stations is structured and operable to deposit one of a plurality of groups of small objects into selected ones of the inter-connected small object cells integrally formed in the at least one small object cassette; and
   a central control system comprising a computer-based controller communicatively connected to at least the conveyor track and each cassette processing station, the central control system structured and operable to control operations of each independently controlled track section of the conveyor track and each cassette processing station.

9. The system of claim 8, wherein each processing station comprises:
   at least one small object counting and parsing subsystem structured and operable to parse a plurality of groups of small objects from a bulk quantity of the small objects, each group of small objects comprising a respective number of small objects stipulated by the central control system; and
   the small object distribution subsystem structured and operable to receive each parsed group of small objects and deposit each parsed group of small objects into a respective one of the small object cells of a respective one of the cassette(s) stipulated by the central control system as the respective cassette is positioned adjacent the small object distribution subsystem via the conveyor track.

10. The system of claim 9, wherein each small object counting and parsing subsystem comprises:
   a bulk small object bin structured and operable to retain the bulk quantity of small objects of a selected type;
   an upper small object bin structured and operable to retain small objects received from the bulk small object bin;
   a decelerator connected to the bulk small object bin by a vacuum conduit structured and operable to transport a plurality of small objects from the bulk small object bin to the decelerator, the decelerator additionally connected to the upper small object bin, wherein the decelerator is structured and operable to decelerate a speed of the small object being transported from the bulk small object bin and deposit them into the upper small object bin;

a small object singulator and counter connected to the upper small object bin, the small object singulator and counter structured and operable to extract small objects from the upper small object bin, count the small objects and parse the small objects into the groups of small objects wherein each group of small objects comprises the respective number of small objects stipulated by the central control system; and a small object queuing assembly structured and operable to receive the groups of small objects from the small object singulator and counter and deposit each group of small objects into the small object distribution subsystem.

11. The system of claim 10, wherein the small object queuing assembly comprises:
a first queuing stage fluidly connected to the small object singulator and counter and structured and operable to receive and temporarily retain each group of small objects from the small object singulator and counter; and
a second queuing stage fluidly connected to the first queuing stage and structured and operable to receive and temporarily retain each group of small objects from the first queuing stage.

12. The system of claim 11, wherein the small object distribution subsystem comprises:
a multi-cell buffer tray comprising a plurality of small object buffer cells;
a small object transport and deposition assembly structured and operable to deposit groups of small objects received from the small object queuing assembly into selected small object buffer cells; and
a sluice tray that is movable between a Closed position and an Open position, wherein when in the Closed position the sluice tray covers the bottom of buffer tray such that groups of small objects deposited in the small object buffer cells are retained within the small object buffer cells, and when in the Open position the sluice tray uncovers the bottom of the buffer tray such that the groups of small objects deposited in the buffer cells are allowed to fall into corresponding small object cells of a small object cassette positioned under the buffer tray via the automated conveyor track.

13. The system of claim 12, wherein the small object deposition assembly comprises at least one third queuing stage mounted to an X-Y transport, the third queuing stage(s) structured and operable to receive and temporarily retain each group of small objects from the second queuing stage and deposit each group of small objects into a respective the selected small object buffer cell, the X-Y transport structured and operable to position the third queuing stage(s) under the second queuing stage and then subsequently over the respective small object buffer cell.

14. The system of claim 13 further comprising at least one cassette sensor structured and operable to sense the location of each cassette as each cassette is transported along the conveyor track, and to communicate with the central control system such that the central control system can monitor and system the location of each cassette as each cassette is transported along the conveyor system.

15. The system of claim 14, wherein the conveyor system further comprises at least one cassette lift structured and operable to at least one of lower each cassette placed on the lift onto the conveyor system, and raise each cassette off the conveyor system for removal by the operator.

16. The system of claim 15 further comprising at least one load-unload station located next to the conveyor system adjacent at least one of the loading and unloading locations, each load-unload station structured and operable to assist in at least one of loading and unloading the cassette(s) onto and off of the conveyor system.

17. The system of claim 16, wherein each load-unload station comprises a pressure pad structured and operable to cause the cassette lift to rise when the pressure pad is activated, and to lower the cassette lift when the operator deactivates the pressure pad.

18. The system of claim 17, wherein each load-unload station further comprises a cassette crate lift structured and operable to raise and lower a cassette crate structured and operable to retain a plurality of small object cassettes.

19. The system of claim 13, wherein at least one of:
the first queuing stage comprises a first stage vibratory wall structured and operable to vibrate to prevent small objects from becoming lodged within the first queuing stage;
the second queuing stage comprises a second stage vibratory wall structured and operable to vibrate to prevent small objects from becoming lodged within the second queuing stage; and
the third small object queuing stage comprises a third stage vibratory wall structured and operable to vibrate to prevent small objects from becoming lodged within the third queuing stage.

20. A high throughput system for sorting a plurality of different small object types into a plurality of cells of at least one small object cassette, said system comprising:
the at least one small object cassette comprising a plurality of small object cells;
an automated conveyor track structured and operable to transport the cassette(s) from a loading location on the conveyor track to a unloading location on the conveyor track;
at least one cassette processing station disposed over the conveyor track such that the conveyor track extends through each cassette processing station and under a small object distribution subsystem of each respective cassette processing station; each cassette processing station comprising:
at least one small object counting and parsing subsystem structured and operable to parse a plurality of groups of small objects from a bulk quantity of the small objects, each group of small objects comprising a respective number of small objects stipulated by the central control system; and
a small object distribution subsystem structured and operable to receive each parsed group of small objects and deposit each parsed group of small objects into a respective one of the small object cells of a respective one of the cassette(s) stipulated by the central control system as the respective cassette is positioned adjacent the small object distribution subsystem via the conveyor track; each small object counting and parsing subsystem comprising
a small object queuing assembly structured and operable to receive the groups of small objects from the small object singulator and counter and deposit each group of small objects into the small object distribution subsystem, each small object queuing assembly comprising:
a first queuing stage fluidly connected to the small object singulator and counter and structured and operable to receive and temporarily retain each group of small objects from the small object singulator and counter; and a second queuing stage fluidly connected to the first queuing stage and structured and operable to receive and temporarily retain each group of small objects from the first queuing stage; and a central control system comprising a computer-based controller communicatively connected to at least the conveyor track and each cassette processing station, the central control system structured and operable to control operations of the conveyor track and each cassette processing station.

* * * * *